(12) United States Patent
Eisenmann et al.

(10) Patent No.: US 11,547,682 B2
(45) Date of Patent: Jan. 10, 2023

(54) USE OF FORMIN AGONISTS IN OVERCOMING BRAIN TUMOR RADIO- AND CHEMO-RESISTANCE BY TARGETING TUMOR MICROTUBES

(71) Applicant: The University of Toledo, Toledo, OH (US)

(72) Inventors: Kathryn Eisenmann, Toledo, OH (US); Krista M. Pettee, Toledo, OH (US); Kathryn Becker, Toledo, OH (US)

(73) Assignee: The University of Toledo, Toledo, OH (US)

( * ) Notice: Subject to any disclaimer, the term of this patent is extended or adjusted under 35 U.S.C. 154(b) by 333 days.

(21) Appl. No.: 16/814,425

(22) Filed: Mar. 10, 2020

(65) Prior Publication Data

US 2020/0289440 A1  Sep. 17, 2020

Related U.S. Application Data

(60) Provisional application No. 62/816,419, filed on Mar. 11, 2019.

(51) Int. Cl.
*A61K 31/175* (2006.01)
*A61P 35/00* (2006.01)
*A61K 45/06* (2006.01)

(52) U.S. Cl.
CPC ............ *A61K 31/175* (2013.01); *A61P 35/00* (2018.01); *A61K 45/06* (2013.01)

(58) Field of Classification Search
CPC .................................................. A61K 31/175
See application file for complete search history.

*Primary Examiner* — Paul V Ward

(74) *Attorney, Agent, or Firm* — MacMillan, Sobanski & Todd, LLC

(57) ABSTRACT

Compositions and methods for inhibiting brain tumor proliferation, or for inhibiting or halting TM formation, invasion, and/or proliferation, or for rendering brain tumor cells sensitive to chemotherapy or radiation, or for treating a brain tumor, or for inducing cell death, involving mDia agonists such as IMM01 and IMM02, are described.

17 Claims, 22 Drawing Sheets

USE OF FORMIN AGONISTS IN OVERCOMING BRAIN TUMOR RADIO- AND CHEMO-RESISTANCE BY TARGETING TUMOR MICROTUBES

RELATED APPLICATIONS

This application claims priority to U.S. Provisional Application No. 62/816,419 filed under 35 U.S.C. § 111(b) on Mar. 11, 2019, the disclosure of which is incorporated herein by reference in its entirety.

STATEMENT REGARDING FEDERALLY SPONSORED RESEARCH

This invention was made with no government support. The government has no rights in this invention.

BACKGROUND

Brain tumors are often highly lethal and difficult to treat with current therapies. Current therapies available to treat many brain tumors include surgery to remove the tumor (resection), radiation (radiotherapy), or chemotherapy. In many types of brain tumors, these therapies fail, and the tumors are called resistant. Overcoming this resistance is paramount to success in treating brain tumors and improving patient outcomes.

High-Grade Glioma (HGG, WHO Grade III-IV) accounts for the majority of adult primary malignant brain tumors. Failure of current therapies to target invasive glioma cells partly explains the minimal survival advantages: invasive tumors lack easily-defined surgical margins, and are inherently more chemo- and radioresistant. Much work centers upon Rho GTPase-mediated glioma invasion, yet downstream Rho effector roles are poorly understood and represent potential therapeutic targets. There is a need in the art for new and improved treatments for high-grade glioma.

SUMMARY

Brain tumors often send out cellular projections when infiltrating and spreading into new areas of the brain. These projections are known as tumor microtubes (TMs). Provided herein is a class of drugs that inhibits these cellular projections in cells from brain tumor patients. These drugs also halt invasion in brain tumor patient primary cells. These drugs may be useful in overcoming radioresistance and chemoresistance in brain tumor patient cells and in the patient themselves.

Provided is a method of inhibiting high-grade glioma (HGG) patient neurosphere invasion, the method comprising administering an effect amount of a mDia agonist to a patient having HGG, and inhibiting HGG neurosphere invasion in the patient. In certain embodiments, the mDia agonist comprises IMM01. In certain embodiments, the mDia agonist comprises IMM02. In certain embodiments, the mDia agonist comprises a combination of IMM01 and IMM02. In certain embodiments, the effective amount ranges from about 10 µM to about 50 µM. In certain embodiments, the HGG is chemoresistant or radioresistant. In certain embodiments, an amoeboid morphology is induced in neurosphere edge cells. In certain embodiments, actin- and tubulin-enriched tumor microtube formation is inhibited. In certain embodiments, the mDia agonist is administered in a combination therapy with a ROCK inhibitor. In certain embodiments, the mDia agonist is an agonist of mDia1. In certain embodiments, the mDia agonist is an agonist of mDia2.

Further provided is a method of halting TM formation, invasion, or proliferation in a patient, the method comprising administering an effect amount of a mDia agonist to a patient having a brain tumor, and halting TM formation, invasion, or proliferation in the patient. In certain embodiments, the mDia agonist comprises IMM01. In certain embodiments, the mDia agonist comprises IMM02. In certain embodiments, the mDia agonist comprises a combination of IMM01 and IMM02. In certain embodiments, the effective amount ranges from about 10 µM to about 50 µM. In certain embodiments, the brain tumor is chemoresistant or radioresistant. In certain embodiments, the mDia agonist is an agonist of mDia1. In certain embodiments, the mDia agonist is an agonist of mDia2.

Further provided is a method of rendering brain tumor cells sensitive to chemotherapy or radiation, the method comprising contacting brain tumor cells with an effective amount of a mDia agonist, and rendering the brain tumor cells sensitive to chemotherapy or radiation. In certain embodiments, the brain tumor cells are in a human. In certain embodiments, the mDia agonist comprises IMM01. In certain embodiments, the mDia agonist comprises IMM02. In certain embodiments, the mDia agonist comprises a combination of IMM01 and IMM02. In certain embodiments, the effective amount ranges from about 10 µM to about 50 µM. In certain embodiments, the mDia agonist is an agonist of mDia1. In certain embodiments, the mDia agonist is an agonist of mDia2.

Further provided is a method of treating a brain tumor, the method comprising administering an effective amount of a mDia agonist to a patient having a brain tumor, and treating the brain tumor. In certain embodiments, the mDia agonist comprises IMM01. In certain embodiments, the mDia agonist comprises IMM02. In certain embodiments, the mDia agonist comprises a combination of IMM01 and IMM02. In certain embodiments, the effective amount ranges from about 10 µM to about 50 µM. In certain embodiments, neurosphere invasion in the patient is disrupted. In certain embodiments, the brain tumor is chemoresistant or radioresistant. In certain embodiments, the mDia agonist is administered in a combination therapy with a ROCK inhibitor. In certain embodiments, the mDia agonist is an agonist of mDia1. In certain embodiments, the mDia agonist is an agonist of mDia2.

Further provided is a method of inducing cell death in brain tumor cells, the method comprising contacting invading brain tumor cells with an effective amount of a mDia agonist and inducing cell death in the invading brain tumor cells. In certain embodiments, the mDia agonist comprises IMM01. In certain embodiments, the mDia agonist comprises IMM02. In certain embodiments, the mDia agonist comprises a combination of IMM01 and IMM02. In certain embodiments, the effective amount ranges from about 10 µM to about 50 µM. In certain embodiments, neurosphere invasion in the patient is disrupted. In certain embodiments, the brain tumor is chemoresistant or radioresistant. In certain embodiments, the mDia agonist is administered in a combination therapy with a ROCK inhibitor. In certain embodiments, the mDia agonist is an agonist of mDia1. In certain embodiments, the mDia agonist is an agonist of mDia2.

BRIEF DESCRIPTION OF THE DRAWINGS

FIG. 1A shows pathological and molecular characteristics of tumors from patient surgeries. NR=not reported. FIG. 1B shows gross images of select individual tumors.

FIG. 1C shows representative images from select patient cell isolations showing the monolayer cells in 2D-culture. Scale bar=400 μm.

FIG. 2A shows Western blots of indicated patient cell line lysates cultured briefly on tissue culture plastic. U87 and U251 cells were used as positive mDia expression controls, as shown in FIGS. 2B-2E. IF of patient-derived HGG cells (Pat9, FIGS. 2B-2C; Pat8, FIGS. 2D-2E) briefly cultured on glass coverslips to visualize mDia1 (green), mDia2 (green), F-actin (phalloidin; red), or nuclei (DAPI; blue).

FIG. 3B shows change in neurosphere invasion graphed as the change in area T0 for Pat8. N>12 neurospheres/condition over three replicate experiments. FIG. 3C shows representative images of Pat9 neurosphere invasion at 0 and 48 h. Scale bars=1000 μm. FIG. 3D shows confocal images of fixed Pat9 48 h invasion assay stained for phalloidin and DAPI and showing the neurosphere edges. Scale bars=50 μm.

FIG. 4A shows invasion assays performed for Pat9 for 48 h and indicated drug treatment was either maintained thereafter (m) or drug was removed and replaced with media alone (r). Assays were then continued through 96 h. Pat9 neurosphere invasion graphed as change in area relative to neurosphere area at the time of embedding (T0). Invasion area was measured 72 or 96 h post-embedding. *$p<0.001$ by ANOVA. FIG. 4B shows representative neurosphere images from Pat9 in FIG. 4A showing invasion assays at 96 either maintained in IMMs or recovered in media after 48 h. Scale bars=1000 μm. FIG. 4C shows Pat9 neurospheres were incubated with the live-dead cell dye Draq7 (red) and phalloidin (green) at the indicated time points, and with or without drug washout, as in FIG. 4A. Scale bars=50 μm.

FIG. 6A shows IF for proteins marking tumor TMs (F-actin (red), Connexin43 (green)), and DAPI to denote nuclei in 2 separate Pat8 neurospheres invading for 96 h. Left-most boxes indicate areas of magnification shown. Scale bar (upper panel)=25 μm; (lower panel 100 μm). FIGS. 6B-6C show tumor TM lengths were measured using Metamorph software from cell nuclei to tumor TM ends. TMs measured from N>196 cells across three replicate experiments. TMs were measured in control (FIG. 6B), or drug washout experiments using 50 μM IMM01 or IMM02 where m=maintained drug and r=washout (FIG. 6C). Data are shown as scatter plots in FIGS. 6B-6C, or histograms (FIGS. 6B', 6C'). FIG. 6C shows tumor TMs measured in control (FIG. 6D) or washout experiments (FIG. 6E), using 50 μM IMM01 or IMM02, where m=maintained drug and r=washout. FIGS. 6D, 6D' show cellular morphologies measured in neurosphere edge cells and EI were calculated by dividing cell long by short axes, where EI=1 is a rounded cell, and E>1 is an elongated cell. N>196 cells across three replicate experiments. Data are shown as scatter plots (FIG. 6D, 6E), or histograms (FIG. 6D', FIG. 6E').

DETAILED DESCRIPTION

Figures 1A, 1B, 1C:
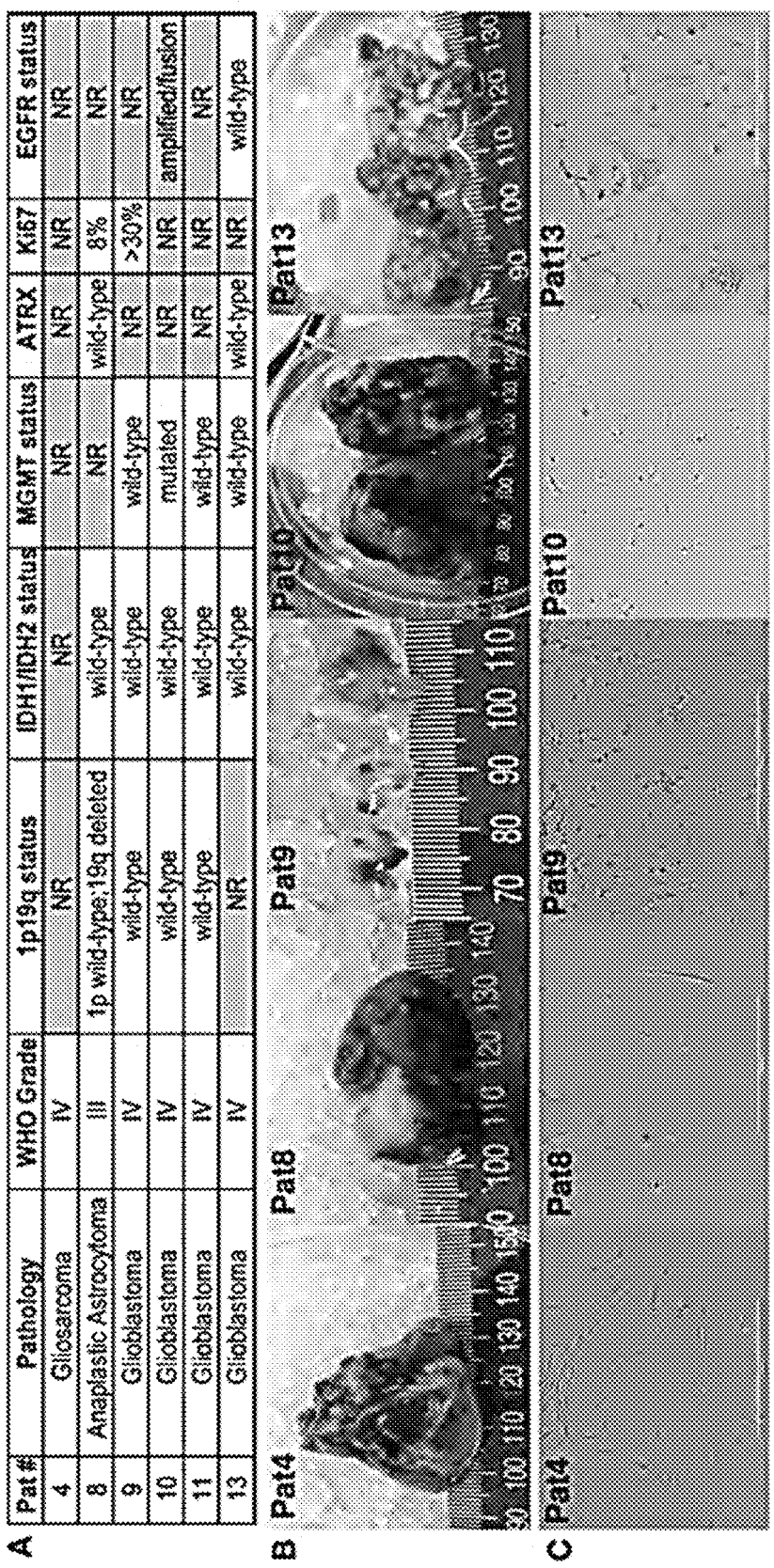
FIGS. 1A-1C.

Throughout this disclosure, various publications, patents, and published patent specifications are referenced by an identifying citation. The disclosures of these publications, patents, and published patent specifications are hereby incorporated by reference into the present disclosure in their entirety to more fully describe the state of the art to which this invention pertains.

The National Cancer Institute SEER program had estimated that >23,000 new cases of brain and other nervous systems cancers would be diagnosed in 2018, and estimated deaths in 2018 were 16,380. Brain tumors can be benign or malignant, and may be derived from primary brain tumors, or may have spread (metastasized) from other tissues in the body. One of the most lethal aspects of brain tumors is their spreading into new areas of unaffected brain. These areas may control vital functions of the body, and thus impeding their function may have deleterious consequences that ultimately can be fatal. In total, the percent of patients surviving 5 years with brain and other nervous system cancers is a dismal 33.2%. Current standard of care is surgical resections, radiation, and/or chemotherapy. In many cases, especially in the cases of high grade gliomas (e.g., WHO grade III-IV, anaplastic astrocytoma, glioblastoma, gliosarcoma), the therapeutic benefits of these treatments are short lived. Complete surgical resection is nearly impossible, and remaining tumor cells invade throughout the brain. Tumor cells nearly always become resistant to chemotherapy and/or radiation through mechanisms that are poorly understood, if at all. Critical clinical aspects to overcome in brain tumor therapy include reducing cellular invasion through the brain (reducing recurrence), chemoresistance, and radioresistance. There are no current clinical applications that can effectively target all three of these clinical roadblocks to effective therapy.

A protein expressed in brain tumor cells called mDia (mDia1-3) has been successfully targeted. In commercially available glioblastoma cell lines, targeting mDia proteins through the use of small molecule mDia agonists called IMMs can effectively halt tumor cell invasion in vitro and in an ex vivo rat brain slice model. The IMMs, which are commercially available, are not toxic to living organisms. Tumor tissue was obtained from high grade glioma surgeries to test if high-grade brain tumor invasion could be halted through IMM incubation. While studying tumor invasion in vitro using structures grown in the lab from high grade glioma patient cells called neurospheres, very long (75-1000 microns) cellular projections that were never seen in cultured cell lines were observed. It was also observed that pre-incubating these neurospheres with IMMs at the time the invasion assays were started dramatically reduced invasion while eliminating the long cellular projections. These projections were enriched in proteins called F-actin, beta-tubulin, and acetylated alpha tubulin. These structures are tumor microtubes (TMs). Evidence in patient-derived xenografts shows that these structures are actin and microtubule enriched, and contain a protein called Connexin43.

Using the Connexin43 antibody, it was confirmed that Connexin43 is in these cellular projections. This confirmed that these structures are tumor TMs, and the small molecule IMM can eliminate them while concurrently inhibiting invasion. As further demonstrated in the examples herein, it has been confirmed in high-grade glioma patient samples that incubating neurospheres that are already invading with IMMs not only halted invasion, eliminated tumor TMs, but also induced cell death without addition of other therapies. However, incubating neurospheres with IMM at the beginning of the invasion assay does not impact viability, but rather, only invasion.

Tumor TMs have been shown in glioblastoma patient-derived cell lines to form an interconnected network when transplanted in mouse brains. This network correlates with enhanced chemoresistance and radiosensitivity in vitro and in vivo (mouse). Genetic manipulation of tumor TM proteins (CAP32, Connexin43) showed that manipulating these proteins could reverse resistance to some effect and slow recurrence at sites of tumor resections. To date, there are no cell permeable small molecules targeting tumor TMs, nor is there a currently known role for mDia formins in patient brain tumor TM formation and/or maintenance. However, as demonstrated in the examples herein, targeting mDia formins with agonists such as IMM agonists or their chemical derivatives will not only halt brain tumor invasion already in progress (slowing the recurrence of tumor at a sight of resection), but will also render remaining tumor cells more sensitive to chemotherapy and radiation. Thus, mDia agonists may be used to halt tumor TM formation, invasion, and proliferation in an already invading tumor population (similar to what one would see clinically in brain tumor patients that are recently diagnosed), but will also render remaining cells sensitive to current therapies of chemotherapies and radiation. Small molecule use, like with IMMs and their analogues, is a more practical and useful approach to delivering therapies to target brain tumor TMs and radio- and chemoresistance than the current genetic approaches. Thus, formin agonists such as IMMs (and their derivatives) may be useful as adjuvant therapies in the treatment of brain tumors to enhance the quality of life and durality of response to the current standard of care therapies.

Non-limiting examples of IMMs include IMM01 and IMM02, which are commercially available. IMM01, also known as 2-[(2,4-dihydroxyphenyl)methylene]-N-(1,1-dimethylethyl)-hydrazinecarbothioamide, has the following structural formula (1):

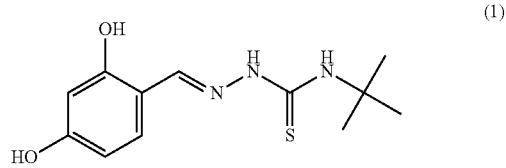 [SMILES: CC(C)(C)NC(=S)N/N=C/c1ccc(O)cc1O]

(1)

IMM02, also known as N1-(tert-butyl)-2-[1-(3,5-difluoro-2-hydroxyphenyl)ethylidene]hydrazine-1-carbothioamide, has the following structural formula (2):

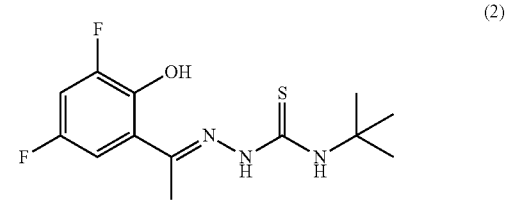 [SMILES: C/C(=N\NC(=S)NC(C)(C)C)c1cc(F)cc(F)c1O]

(2)

Pharmaceutical compositions of the present disclosure comprise an effective amount of a mDia agonist (an "active" compound), and/or additional agents, dissolved or dispersed in a pharmaceutically acceptable carrier. The preparation of a pharmaceutical composition that contains at least one compound or additional active ingredient will be known to those of skill in the art in light of the present disclosure, as exemplified by Remington's Pharmaceutical Sciences, 2003, incorporated herein by reference. Moreover, for animal (e.g., human) administration, it is understood that preparations should meet sterility, pyrogenicity, general safety, and purity standards as required by FDA Office of Biological Standards.

A composition disclosed herein may comprise different types of carriers depending on whether it is to be administered in solid, liquid or aerosol form, and whether it need to be sterile for such routes of administration as injection. Compositions disclosed herein can be administered intravenously, intradermally, transdermally, intrathecally, intraarterially, intraperitoneally, intranasally, intravaginally, intrarectally, intraosseously, periprosthetically, topically, intramuscularly, subcutaneously, mucosally, intraosseosly, periprosthetically, in utero, orally, topically, locally, via inhalation (e.g., aerosol inhalation), by injection, by infusion, by continuous infusion, by localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 2003, incorporated herein by reference).

The actual dosage amount of a composition disclosed herein administered to an animal or human patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In certain embodiments, a composition herein and/or additional agent is formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsules, they may be compressed into tablets, or they may be incorporated directly with the food of the diet.

In further embodiments, a composition described herein may be administered via a parenteral route. As used herein, the term "parenteral" includes routes that bypass the alimentary tract. Specifically, the pharmaceutical compositions disclosed herein may be administered, for example but not limited to, intravenously, intradermally, intramuscularly, intraarterially, intrathecally, subcutaneous, or intraperitoneally (U.S. Pat. Nos. 6,753,514, 6,613,308, 5,466,468, 5,543,158; 5,641,515, and 5,399,363 are each specifically incorporated herein by reference in their entirety).

Solutions of the compositions disclosed herein as free bases or pharmacologically acceptable salts may be prepared in water suitably mixed with a surfactant, such as hydroxypropylcellulose. Dispersions may also be prepared in glycerol, liquid polyethylene glycols and mixtures thereof, and in oils. Under ordinary conditions of storage and use, these preparations may contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In some cases, the form must be sterile and must be fluid to the extent that easy injectability exists. It should be stable under the conditions of manufacture and storage and should be preserved against the contaminating action of microorganisms, such as bacteria and fungi. The carrier can be a solvent or dispersion medium containing, for example, water, ethanol, polyol (i.e., glycerol, propylene glycol, liquid polyethylene glycol, and the like), suitable mixtures thereof, and/or vegetable oils. Proper fluidity may be maintained, for example, by the use of a coating, such as lecithin, by the maintenance of the required particle size in the case of dispersion, and/or by the use of surfactants. The prevention of the action of microorganisms can be brought about by various antibacterial and antifungal agents, such as, but not limited to, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption such as, for example, aluminum monostearate, or gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

Sterile injectable solutions are prepared by incorporating the compositions in the required amount in the appropriate solvent with various other ingredients enumerated above, as required, followed by filtered sterilization. Generally, dispersions are prepared by incorporating the various sterilized compositions into a sterile vehicle which contains the basic dispersion medium and the required other ingredients from those enumerated above. In the case of sterile powders for the preparation of sterile injectable solutions, some methods of preparation are vacuum-drying and freeze-drying techniques which yield a powder of the active ingredient plus any additional desired ingredient from a previously sterile-filtered solution thereof. A powdered composition is combined with a liquid carrier such as, but not limited to, water or a saline solution, with or without a stabilizing agent.

In other embodiments, the compositions may be formulated for administration via various miscellaneous routes, for example, topical (i.e., transdermal) administration, mucosal administration (intranasal, vaginal, etc.) and/or via inhalation.

Pharmaceutical compositions for topical administration may include the compositions formulated for a medicated application such as an ointment, paste, cream, or powder. Ointments include all oleaginous, adsorption, emulsion, and water-soluble based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones, and luarocapram. Possible bases for compositions for topical application include polyethylene glycol, lanolin, cold cream, and petrolatum, as well as any other suitable absorption, emulsion, or water-soluble ointment base. Topical preparations may also include emulsifiers, gelling agents, and antimicrobial preservatives as necessary to preserve the composition and provide for a homogenous mixture. Transdermal administration of the compositions may also comprise the use of a "patch." For example, the patch may supply one or more compositions at a predetermined rate and in a continuous manner over a fixed period of time.

In certain embodiments, the compositions may be delivered by eye drops, intranasal sprays, inhalation, and/or other aerosol delivery vehicles. Methods for delivering compositions directly to the lungs via nasal aerosol sprays has been described in U.S. Pat. Nos. 5,756,353 and 5,804,212 (each specifically incorporated herein by reference in their entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts and could be employed to deliver the compositions described herein. Likewise, transmucosal drug delivery in the form of a polytetrafluoroetheylene support matrix is described in U.S. Pat. No. 5,780,045 (specifically incorporated herein by reference in its entirety), and could be employed to deliver the compositions described herein.

It is further envisioned the compositions disclosed herein may be delivered via an aerosol. The term aerosol refers to a colloidal system of finely divided solid or liquid particles dispersed in a liquefied or pressurized gas propellant. The typical aerosol for inhalation consists of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight, and the severity and response of the symptoms.

In particular embodiments, the compounds and compositions described herein are useful for inhibiting or halting neurosphere invasion. Furthermore, the compounds and compositions herein can be used in combination therapies. That is, the compounds and compositions can be administered concurrently with, prior to, or subsequent to one or more other desired therapeutic or medical procedures or drugs.

One non-limiting example of a combination therapy is the combination of a mDia agonist and a Rho-associated protein kinase (ROCK) inhibitor. However, many other combination therapies are possible and encompassed within the scope of the present disclosure. The particular combination of therapies and procedures in the combination regimen will take into account compatibility of the therapies and/or procedures and the desired therapeutic effect to be achieved. Combination therapies include sequential, simultaneous, and separate administration of the active compound in a way that the therapeutic effects of the first administered procedure or drug is not entirely disappeared when the subsequent procedure or drug is administered.

EXAMPLES

Targeting the mDia Formin-Assembled Cytoskeleton is an Effective Anti-Invasion Strategy in Adult High-Grade Glioma Patient-Derived Neurospheres Roles for the mammalian Diaphanous (mDia)-related formin family of Rho effectors have emerged in invasive/metastatic disease. mDias assemble linear F-actin to promote protrusive cytoskeletal structures underlying tumor cell invasion. Small molecule mDia intramimic (IMM) agonists induced mDia functional activities including F-actin polymerization. mDia agonism inhibited polarized migration in Glioblastoma (WHO Grade IV) cells in three-dimensional (3D) in vitro and rat brain slice models. In these examples, whether the clinically-relevant high-grade glioma patient-derived neurosphere invasion is sensitive to formin agonism is evaluated. Surgical HGG samples were dissociated, briefly grown as monolayers, and spontaneously formed non-adherent neurospheres. IMM treatment dramatically inhibited HGG patient neurosphere invasion both at neurosphere embedding and mid-invasion assay, inducing an amoeboid morphology in neurosphere edge cells, while inhibiting actin- and tubulin-enriched tumor microtube formation. Thus, mDia agonism effectively disrupts multiple aspects of patient-derived HGG neurosphere invasion.

High-Grade Gliomas (HGG, World Health Organization (WHO) Grade III-IV) account for the majority of adult primary malignant brain tumors. HGGs remain an extremely deadly disease. The most aggressive among these tumors is glioblastoma and its morphological sub-variant gliosarcoma (GBM and GSM respectively, WHO Grade IV), along with astrocytoma 46 (WHO grade III). Patients with GBM face an average survival time of 15 months and a 5-year survival rate of 5.5%. Advances in neurosurgery and anti-tumor technologies have not meaningfully impacted survival, and the standard of care has remained unchanged for over ten years: cytoreductive surgery, radiation, and adjuvant temozolomide. In light of these realities, the demand for better treatment options is clear.

One of the greatest clinical challenges in treating adult HGG is the invasive nature of the disease. Early radical attempts to treat GBM with complete hemispherectomy of the affected side eventually saw contralateral recurrence. At a single cell level HGG migrates startlingly great distances away from primary tumors. This migration facilitates resistance to targeted radiation therapy, which is only further complicated by observations that indicate ionizing radiation may promote cell invasion. Drugs that target GBM's angiogenic capacity also increased cellular invasion. These factors culminate to present a target that is largely invisible and always on the move.

Previous studies showed that traditional single cell assays have limitations relative to 3D multicellular modeling of HGG invasiveness. In contrast, compact 3D multi-cellular neurospheres offer a better in vitro model of the tumor microenvironment characterized by complex cell-cell and cell-matrix interactions. These interactions critically influence chemoresistance mechanisms and maintenance of a self-renewing cancer stem-like cell phenotype characteristic of clinical HGG and notably absent in commercially-available HGG cell lines. This more accurate match of experimental model to clinical behavior is important as HGG stem-like cells and their role in primary tumor chemoresistance and invasion are targeted.

Tumor cells generate force to propel them into the surrounding brain architecture. Tumor cell invasion is highly dependent on dynamic remodeling of the actin and microtubule cytoskeleton systems. Global cytoskeleton targeting for anti-invasive cancer therapy was validated (i.e., Taxol) in several cancers. In GBM, newly-identified cytoskeleton-enriched structures called tumor microtubes (TMs) were shown to correlate with invasiveness in patient-derive cell line xenografts. Tumor TMs are enriched in F-actin, microtubules, myosin IIa, and the gap junction protein Connexin43. Interestingly, tumor TMs that formed in patient-derived GBM cell lines xenografted into mice were long-lived (days-weeks), and often times extended hundreds of μm in length within the brain microenvironment, thus differentiating them from other cytoskeleton-enriched structures such as tunneling nanotubes. Targeting the protein machinery in tumor TMs (i.e., Connexin43, GAP-43) by knockdown approaches induced both markedly increased survival, radio- and chemosensitivity through loss of the GBM tumor TM network. Furthermore, tumor TM induction correlated with increased GBM cell invasion within the brain, possibly through observed activation of Rho family GTPases. It remains unclear whether targeting Rho GTPases and their downstream effectors would alter tumor TM formation in GBM.

In GBM, differential expression of Rho GTPase family members dictates invasive strategies. Rho GTPases are molecular switches that mediate their effects through interaction with downstream effectors. One family of Rho effectors is the mammalian Diaphanous-related formins (mDia1-3), which are encoded by the DIAPH/DRF genes. mDia formins are nanomachines that nucleate and elongate linear actin filaments through activation of conserved Formin Homology 2 domains (FH2). The mDia FH2 domain is flanked by the Dia-autoregulatory domain (DAD) and the Dia-inhibitory domain (DID). DAD and DID intramolecular interactions underlie an autoinhibited conformation that sterically hinders FH2 association with actin monomers. Upon interaction with Rho GTPases, the DAD-DID bonds dissociate, expose the FH2 domain, and promote F-actin nucleation and polymerization. mDias also associate with and stabilize the microtubule cytoskeleton. Targeting mDia has been validated as an anti-invasive cancer therapy in in vitro GBM, breast, ovarian, and colon human cancer models.

mDia protein function can be pharmacologically manipulated with small molecules. Antagonism has been broadly studied with the small molecule inhibitor of FH2 domain (SMIFH2), which blocks mDia-mediated F-actin assembly. SMIFH2 downregulated p53 expression, and is cardiotoxic to developing zebrafish embryos at concentrations above the $IC_{50}$ suppressing invasion. mDia1 knockout was associated with T-cell dysfunction and development of myelodysplastic syndromes. Alternatively, mDia agonism with the small molecules Intramimic-01 and Intramimic-02 (IMM01 and IMM02) relieved mDia autoinhibition to induce F-actin polymerization. IMM agonism represents an anti-invasion strategy in cultured GBM cell lines that is superior to SMIFH2 antagonism by blocking directional and random migration in both spheroids in vitro, and invasion into rat brain slices ex vivo. mDia agonism with IMMs have a significantly lower toxicity threshold in vivo relative to SMIFH2 antagonism.

In the presen examples, the efficacy of mDia agonism with IMMs as an effective anti-invasion strategy in a clinically relevant model of patient-derived primary HGG cells that spontaneously grow as neurospheres were evaluated. mDia formins were enriched in primary HGG tumors. Treatment of patient-derived HGG neurospheres with IMMs suppressed multiple aspects of tumor cell invasion, including single cell migration from neurosphere cores, and directed an amoeboid morphological switch in neurosphere edge cells. Interestingly, the formation/maintenance of long actin- and microtubule-enriched pro-invasion tumor TMs were inhibited in response to mDia agonism in neurospheres. Collectively, these data indicate that IMM-based mDia agonism may be useful for therapeutically targeting multiple mechanisms underlying adult HGG cellular invasion.

Results

Patient-Derived Central Nervous System Tumor (CNS) Cell Isolation, Characterization, and Culture De-identified suspected high-grade glioma surgical samples were collected and immediately processed to a single cell suspension. CNS tumors were confirmed with pathological analysis (FIGS. 1A-1B). Molecular characterization of tumors was performed, assessing IDH1/IDH2 mutational status (mutations present in a majority of low-grade diffuse gliomas or secondary gliomas and indicative of better outcome and survival); 1p/19q co-deletion (differentiates oligodendroglioma from astrocytic lineages and predicts greater chemosensitivity); MGMT methylation (predicts overall survival due to increased chemosensitivity); Ki67 index; and ATRX status (differentiates astrocytoma from oligodendrocyte lineages and used as glioma molecular sub-classification marker). Tumor cells from cell suspensions were initially plated upon tissue culture plastic. HGGs including Anaplastic Astrocytoma, Glioblastoma, and the GBM sub-variant Gliosarcoma consistently yielded rigorous long-term cultures (FIG. 1C).

Figure 7:
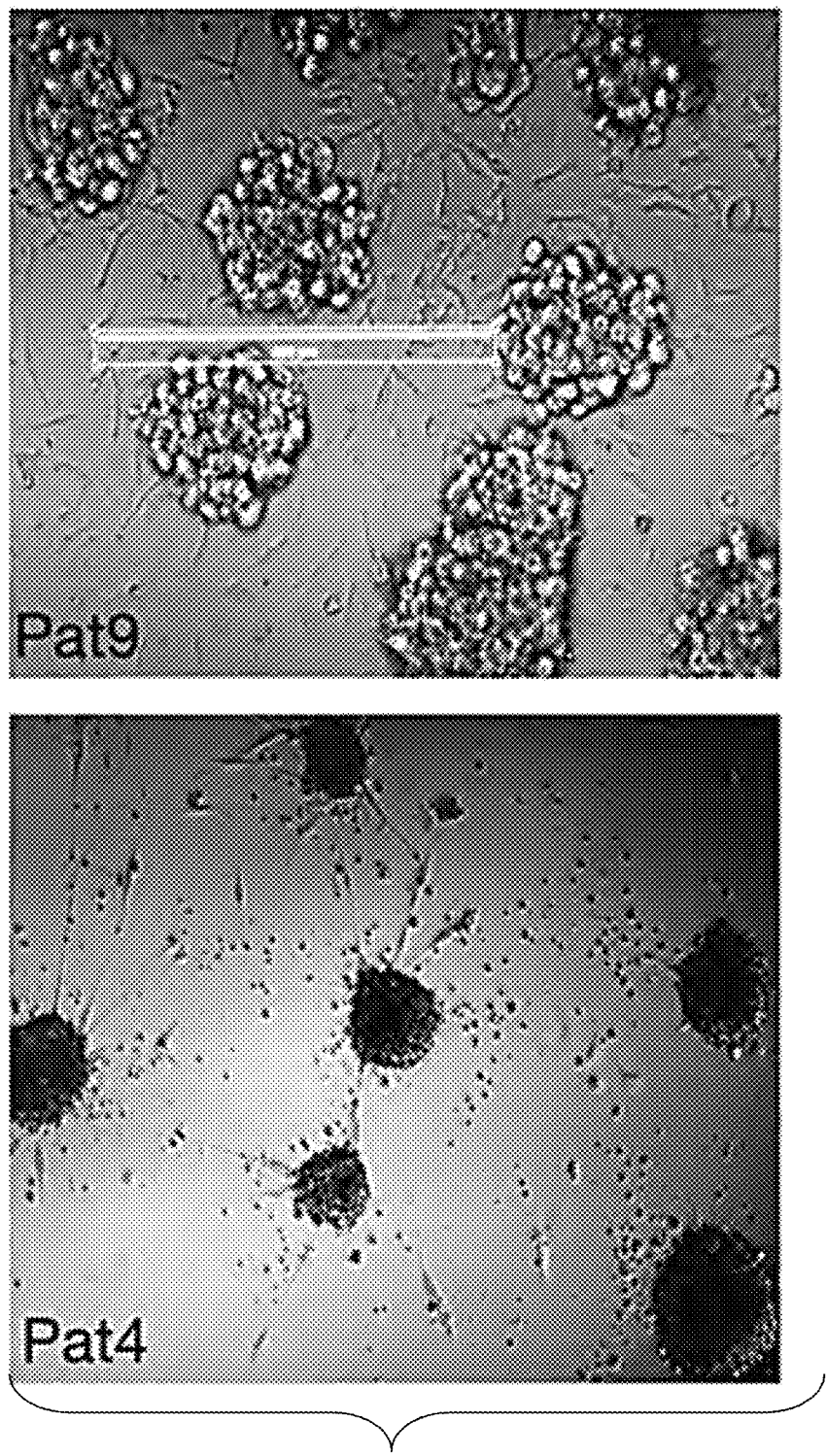
FIG. 7: Patient-derived HGG neurospheres spontaneously form. Neurospheres formed from Pat9 (upper) and Pat4 (lower) primary cultures within days of plating as monolayers. Neurospheres were collected and propagated in suspension culture.

In most patient-derived HGGs, cells spontaneously formed 3D neurospheres (FIG. 7), which detached and were propagated in low-attachment suspension culture (i.e., Patient samples-4 (Pat4),-8 (Pat8),-9 (Pat9), and -13 (Pat13)) for remaining studies.

mDia Formins are Differentially Expressed in Human HGG Patient Tumors

Figure 2A:
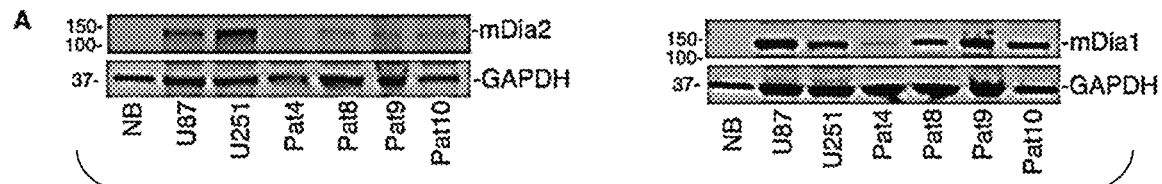
FIGS. 2A-2E.
Figures 2B, 2C, 2D, 2E:
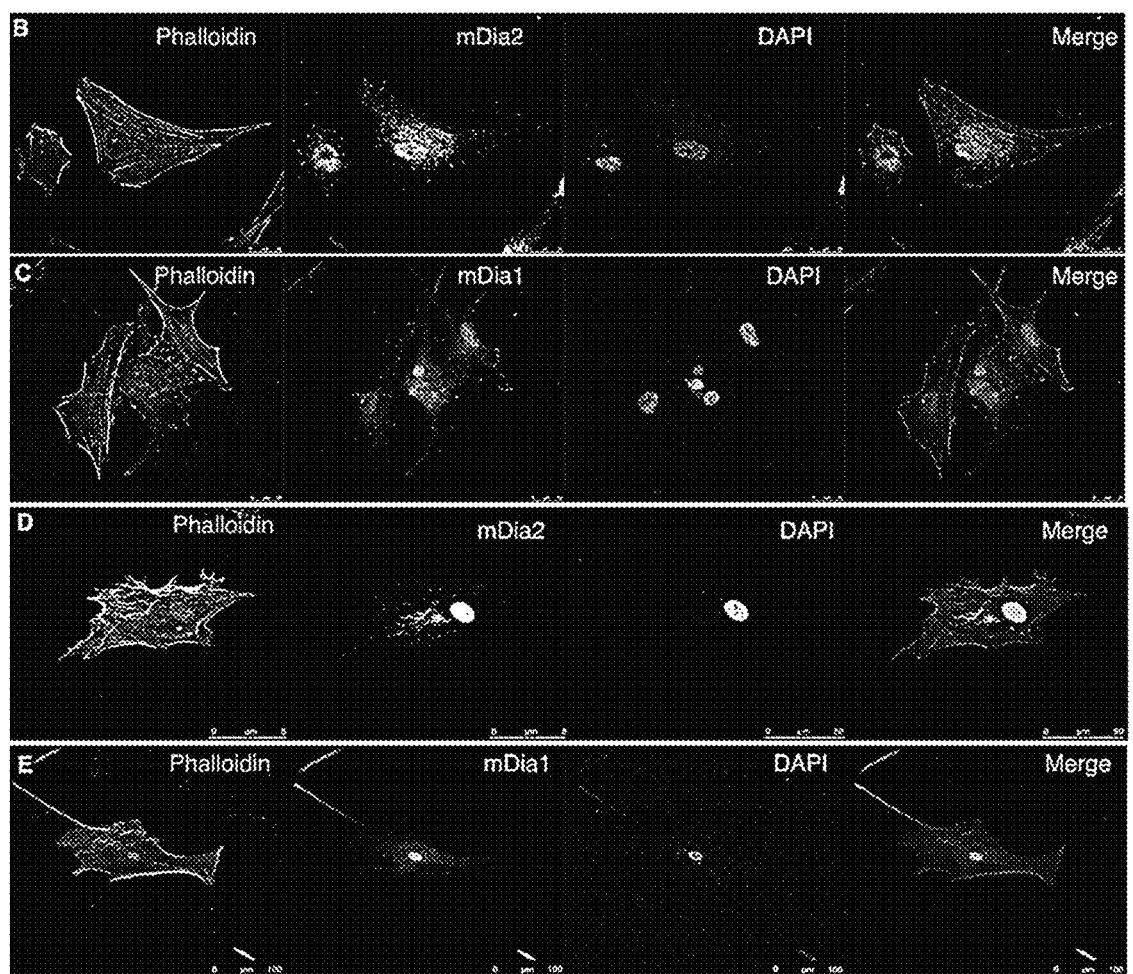

DIAPH3 was modestly yet significantly upregulated in grades II-IV gliomas, relative to normal brain and was expressed in U87 and U251 glioma cells. Western-blotting lysates from patient-derived cell monolayers (Pat4, 8, 9, 10) for mDia1 and mDia2 (FIG. 2A) showed both proteins expressed to varying degrees. This was confirmed by immunofluorescence (IF) to visualize mDia2 and mDia1 (FIG. 2B) in Pat9 (upper panel) and Pat8 (lower panel). mDia2 spatial localization for Pat9 and Pat8 cells was nuclear and perinuclear. mDia1 was both nuclear and diffusely cytoplasmic.

mDia Agonism Inhibits Patient-Derived Neurosphere Invasion

Figure 3A:
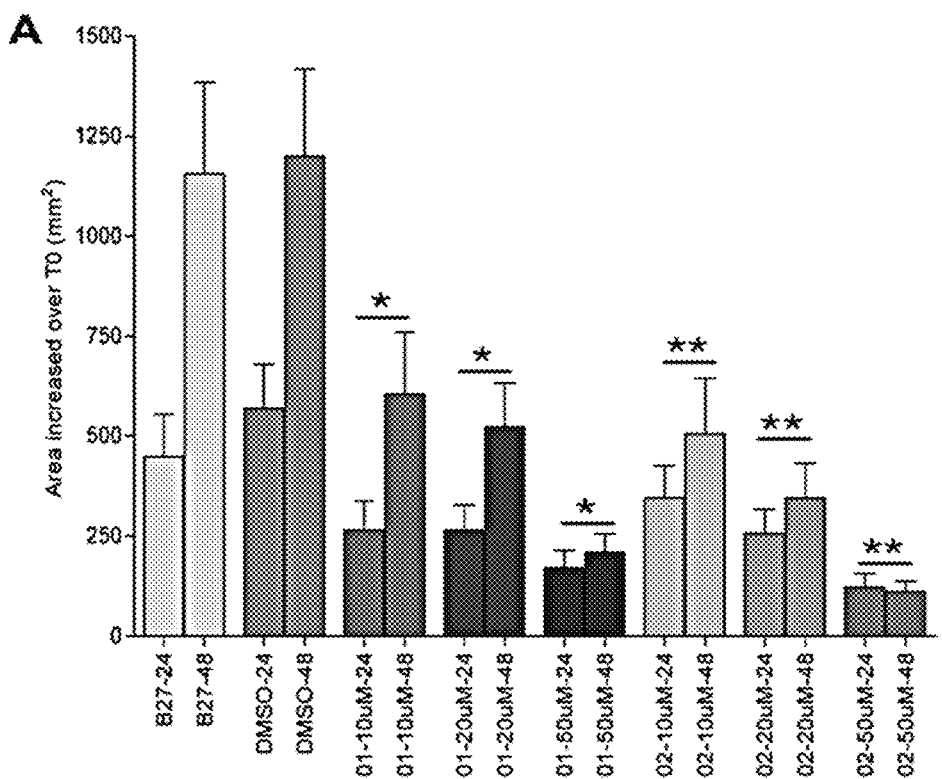
FIGS. 3A-3D: mDia agonists halt HGG patient neurosphere invasion. Neurospheres were formed and embedded in matrigel. Neurosphere areas were measured at embedding (T0), at 24 h and 48 h invasion (FIG. 3A). Change in neurosphere invasion graphed as the change in area over T0 for Pat9. N>12 neurospheres/condition over three replicate experiments. p values are relative to the corresponding time point in B27-treated control invasion assays where *$p<0.0001$; #$p<0.003$.
Figure 3B:
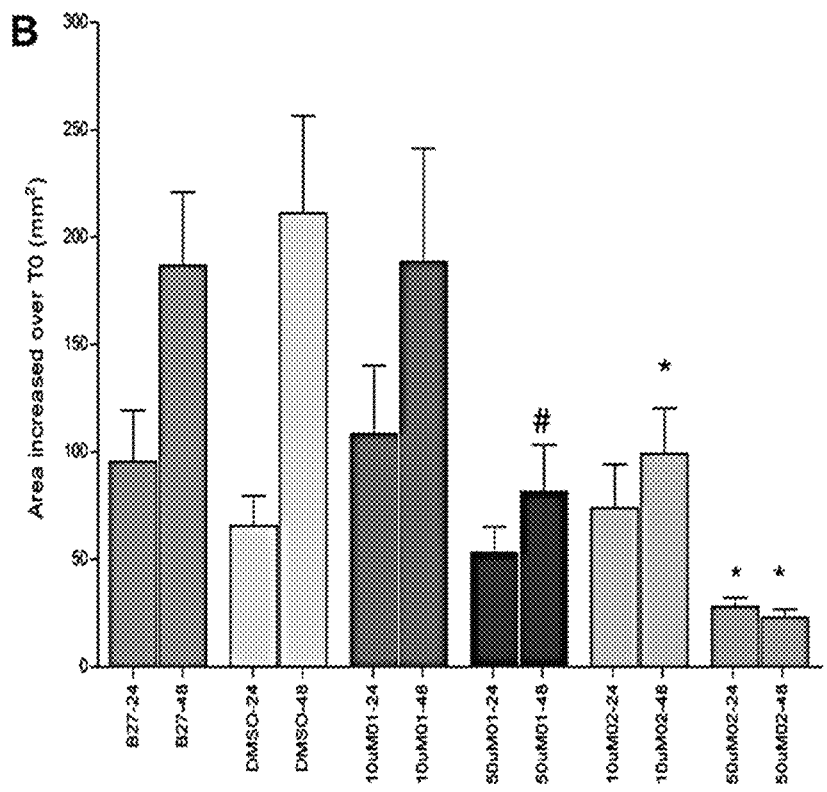
Figure 3C:
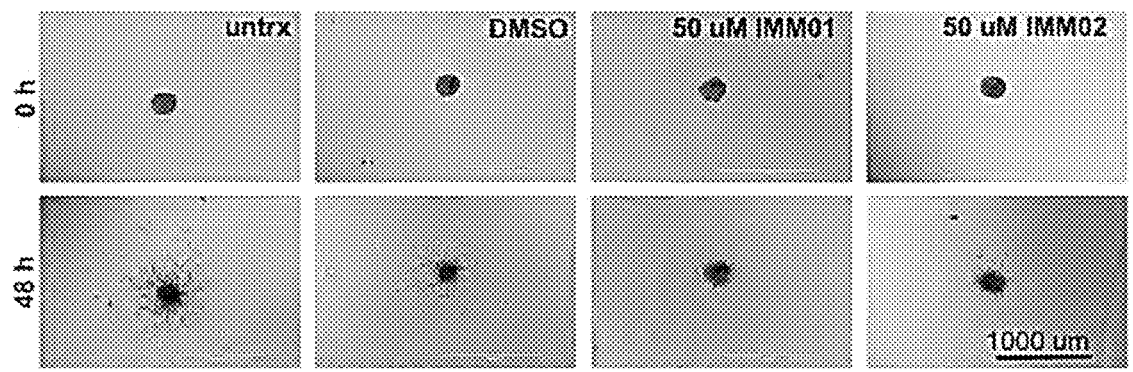
Figure 3D:
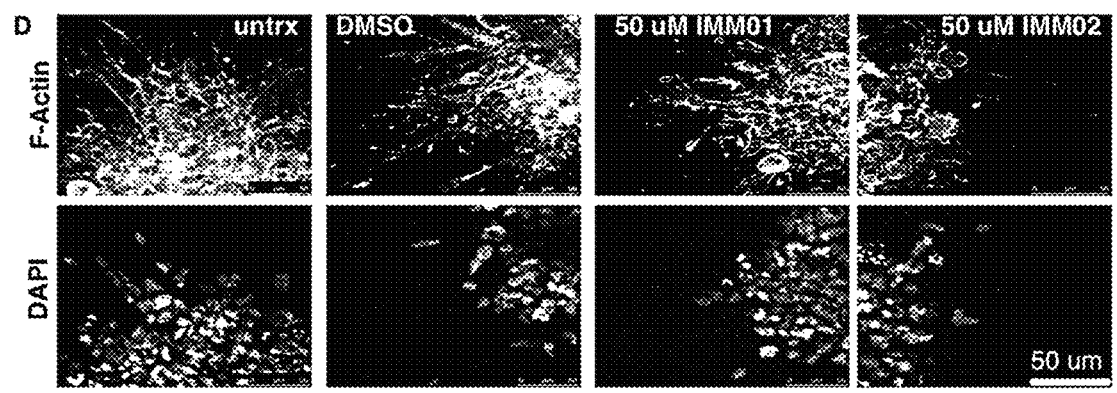

Pat8 and Pat9 HGG neurospheres were embedded in matrigel and allowed to invade. At embedding, neurospheres were treated with 10-50 μM IMM01 or IMM02 and refreshed daily. Images were captured at embedding (T0) and every 24 h. Invasion area was calculated as increase in area over T0 Pat9 or Pat8 neurosphere areas (FIGS. 3A-3B, respectively). Both Pat9 and Pat8 neurospheres robustly invaded through 48 h, similar to control vehicle-treated neurospheres. However, both IMM01 and IMM02 significantly halted invasion within 24 h relative to controls, and inhibition was maintained through 48 h (FIGS. 3C-3D).

Patient-Derived Neurosphere Invasion Inhibition Via mDia Agonism is Reversible

Figure 4A:
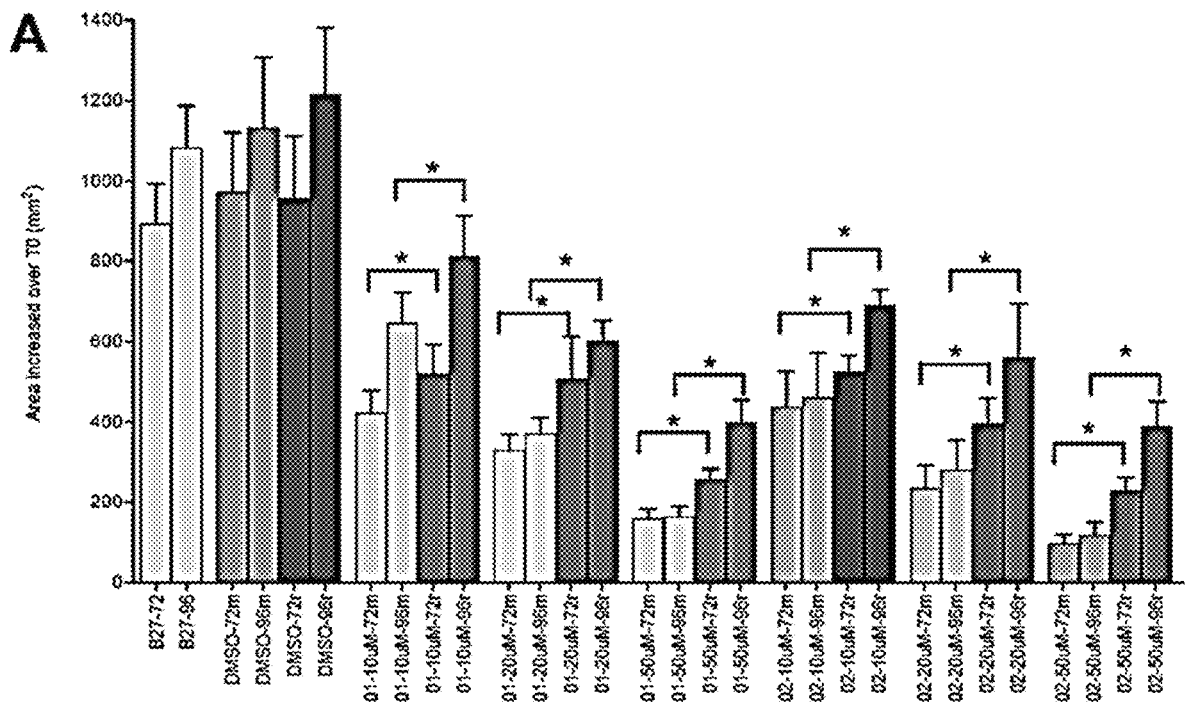
FIGS. 4A-4C: HGG patient neurosphere invasion is recovered upon IMM drug washout.
Figure 4B:
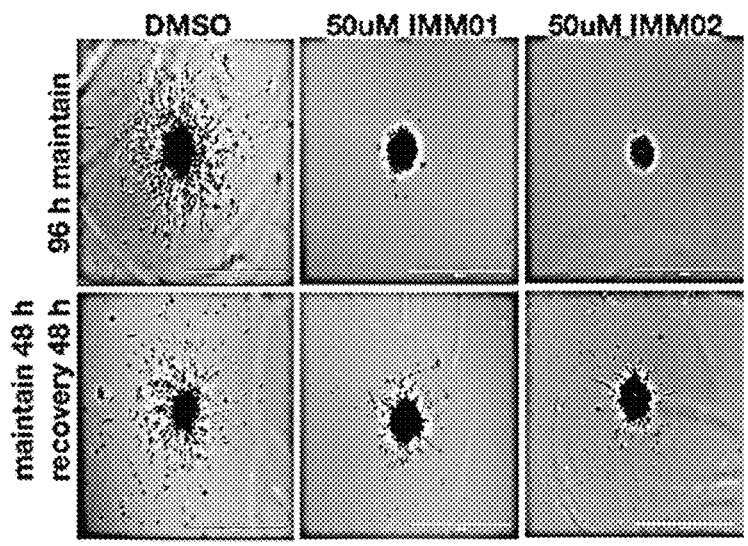
Figure 4C:
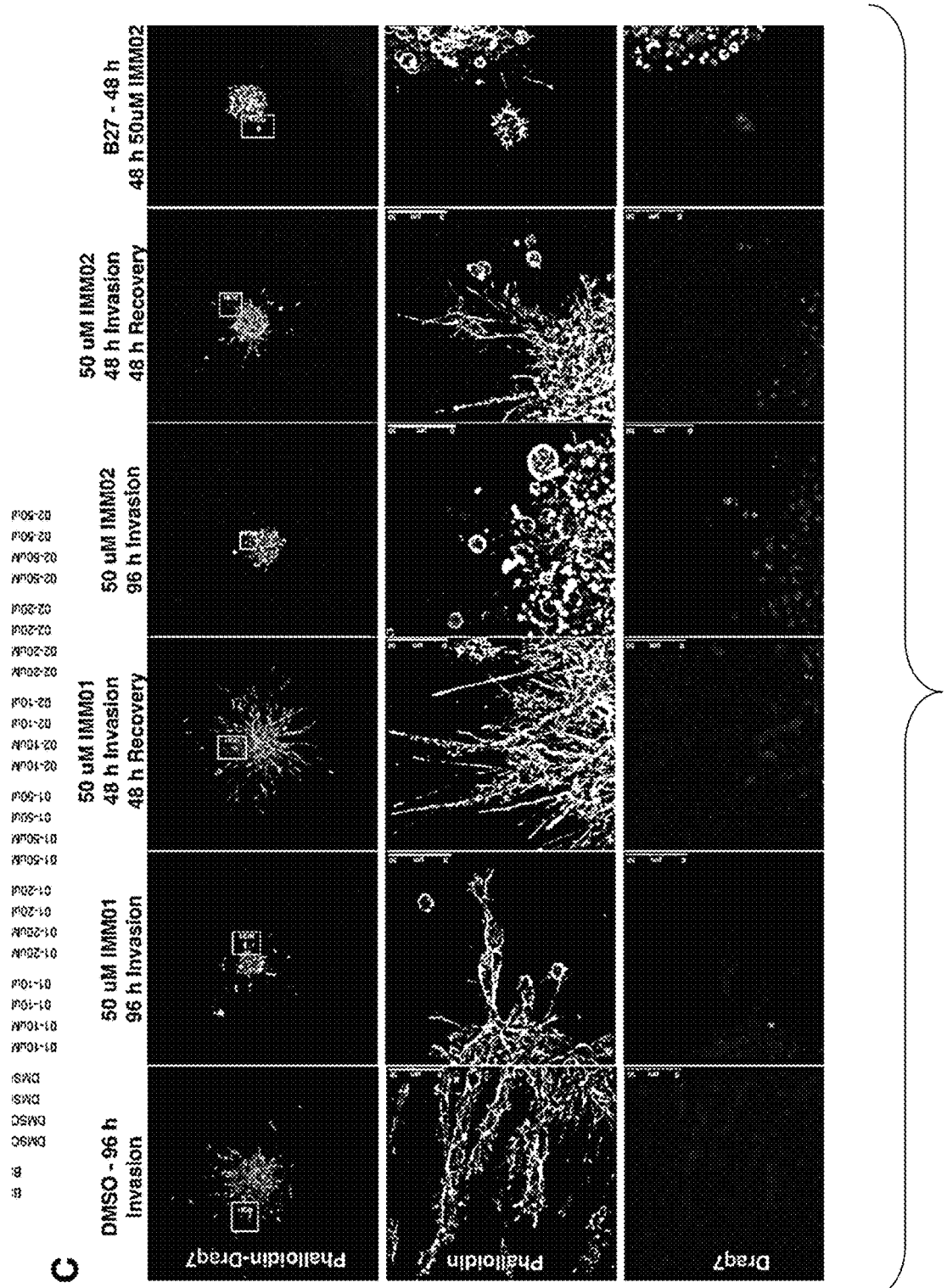
Figure 5A:
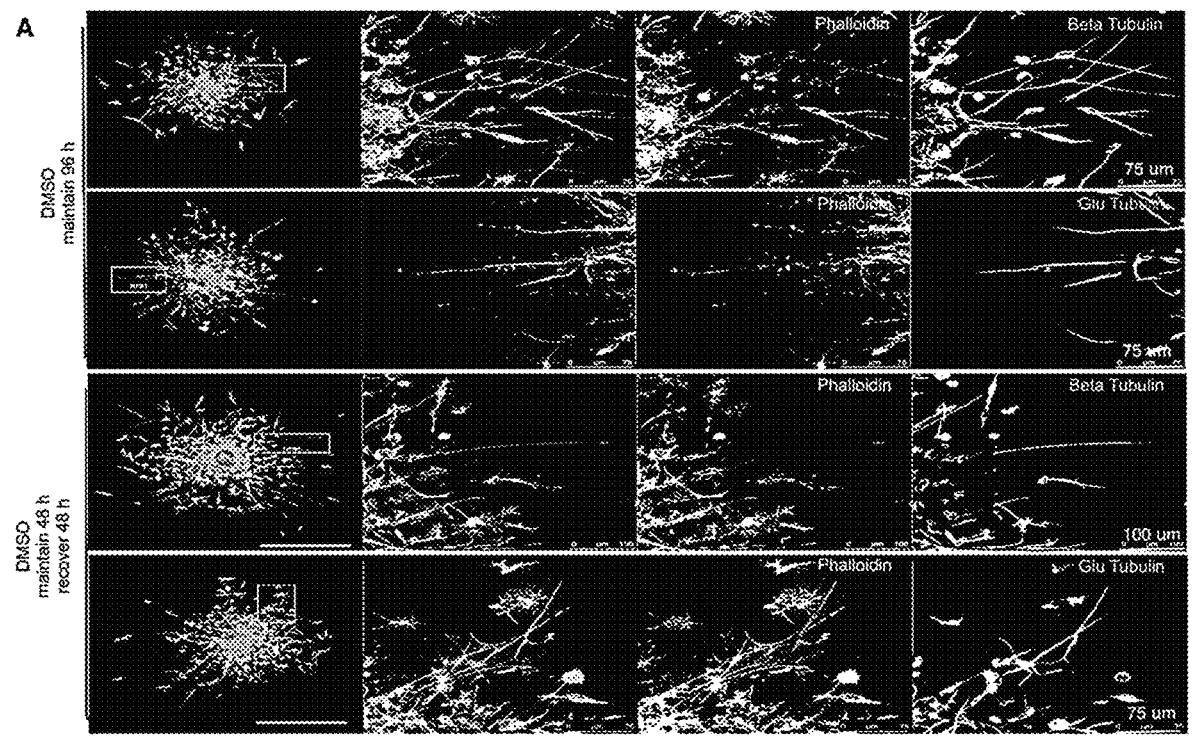
FIGS. 5A-5B: mDia agonism prevents HGG cell cytoskeleton projections. Confocal imaging of fixed Pat9 invasion assays shown in FIGS. 4A-4C. Imaging was for F-actin (green), β-tubulin, or de-tyrosinated α-tubulin (glu-tubulin) (red) (at the edge of FIG. 5A), DMSO, or 50 μM IMM02-treated neurospheres (FIG. 5B). Images are z-stack projections at 96 h of invasion. Treatments were either maintained for 96 h or removed at 48 h of invasion and replaced with media alone for the remaining 48 h of invasion.
Figure 8:
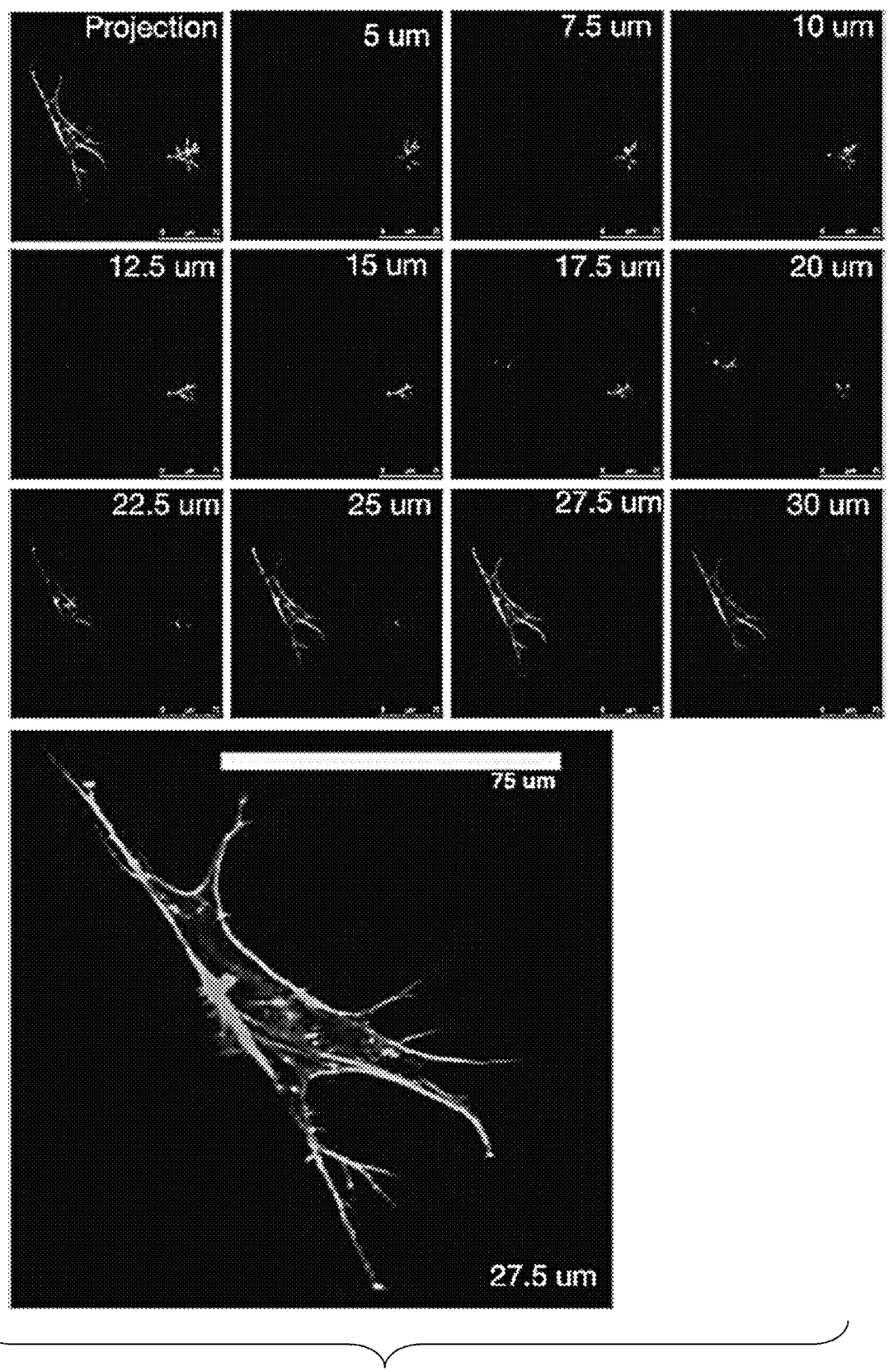
FIG. 8: Actin enrichment in migrating Pat9 neurosphere cells. Pat9 neurospheres were allowed to invade for 96 h and were stained for F-actin (phalloidin) to visualize the F-actin cytoskeleton. Upper left is Z-projection from confocal stack, while remaining images are serial optical slices of the field. Left image is enlargement of the 27.5 μm slice to show details of cytoskeletal projections and stress fibers.

It was previously shown in U87 spheroids that IMM invasion blockade was reversible. Whether IMM anti-invasion effects were reversible was assessed (FIGS. 4A-4B). Pat9 neurospheres were incubated with vehicle or IMMs for 48 h. Drug washouts were then performed with drug-free media and invasion continued for 48 h. As before, IMM removal released invasion suppression relative to neurospheres held in IMMs for 96 h. The live-dead cell dye Draq7 was then used on invading neurospheres treated with IMMs. IMM-treated Pat9 neurospheres revealed no evidence of apoptosis (as they excluded the dye) when agonists were continuously incubated with neurospheres starting at the time of embedding and maintained for 96 h. Unexpectedly, when started at 48 h post-invasion in B27-treated control invading neurospheres, IMM treatment for 48 h thereafter induced robust cell death (FIG. 4C).

mDia Agonism Halts Formation of F-Actin and Tubulin-Enriched Tumor Microtubes (TMs) in Invading HGG Neurospheres IF was performed on fixed Pat9 neurospheres treated with or without IMMs for 96 h (FIGS. 5A-5B, respectively). mDia1, mDia2, F-actin, β-tubulin, or de-tyrosinated β-tubulin (glu-tubulin) were visualized (to assess stabilized microtubules). Invaded control neurospheres had diffuse invasive fronts, with extensive symmetrical invasion away from the central neurosphere core. Both mDia1 and mDia2 were diffusely cytoplasmic. The invasive front of control treated neurospheres revealed a heterogenous mixture of invading cells of various morphologies (elongated, round, stellate). Some cells were enriched in traditional parallel lamellar actin stress fibers and others with numerous radial F-actin-enriched filopodia-like structures (FIG. 8).

Figure 5B:
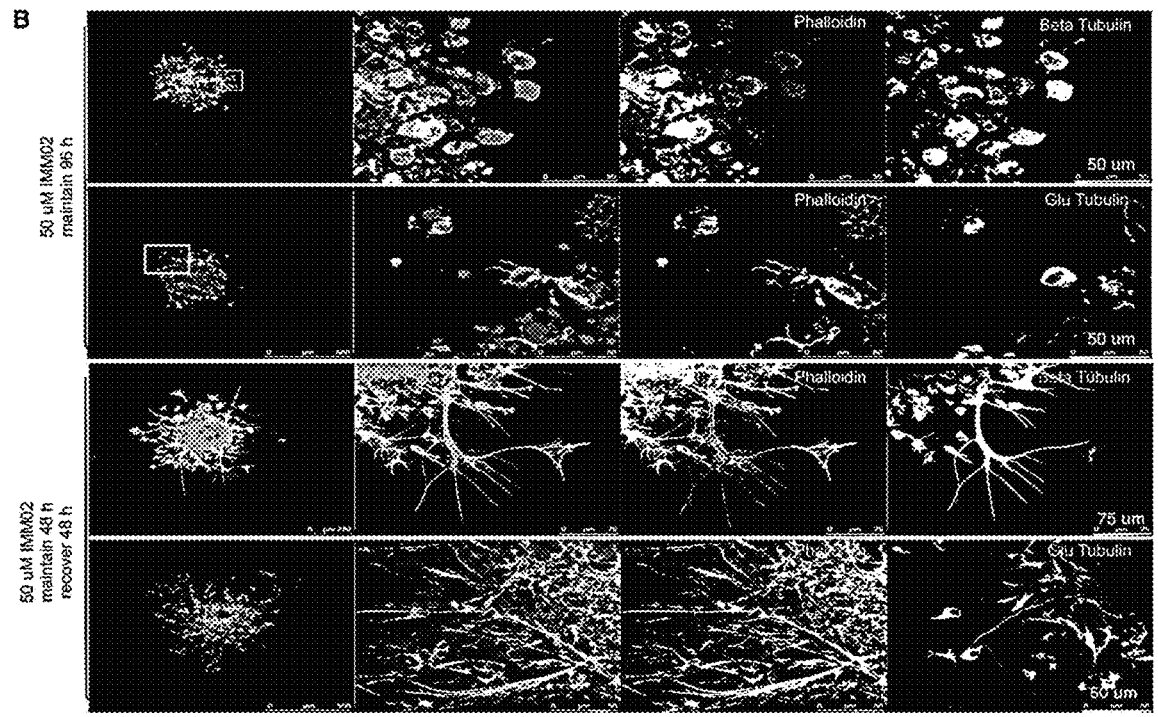
Figure 9A:
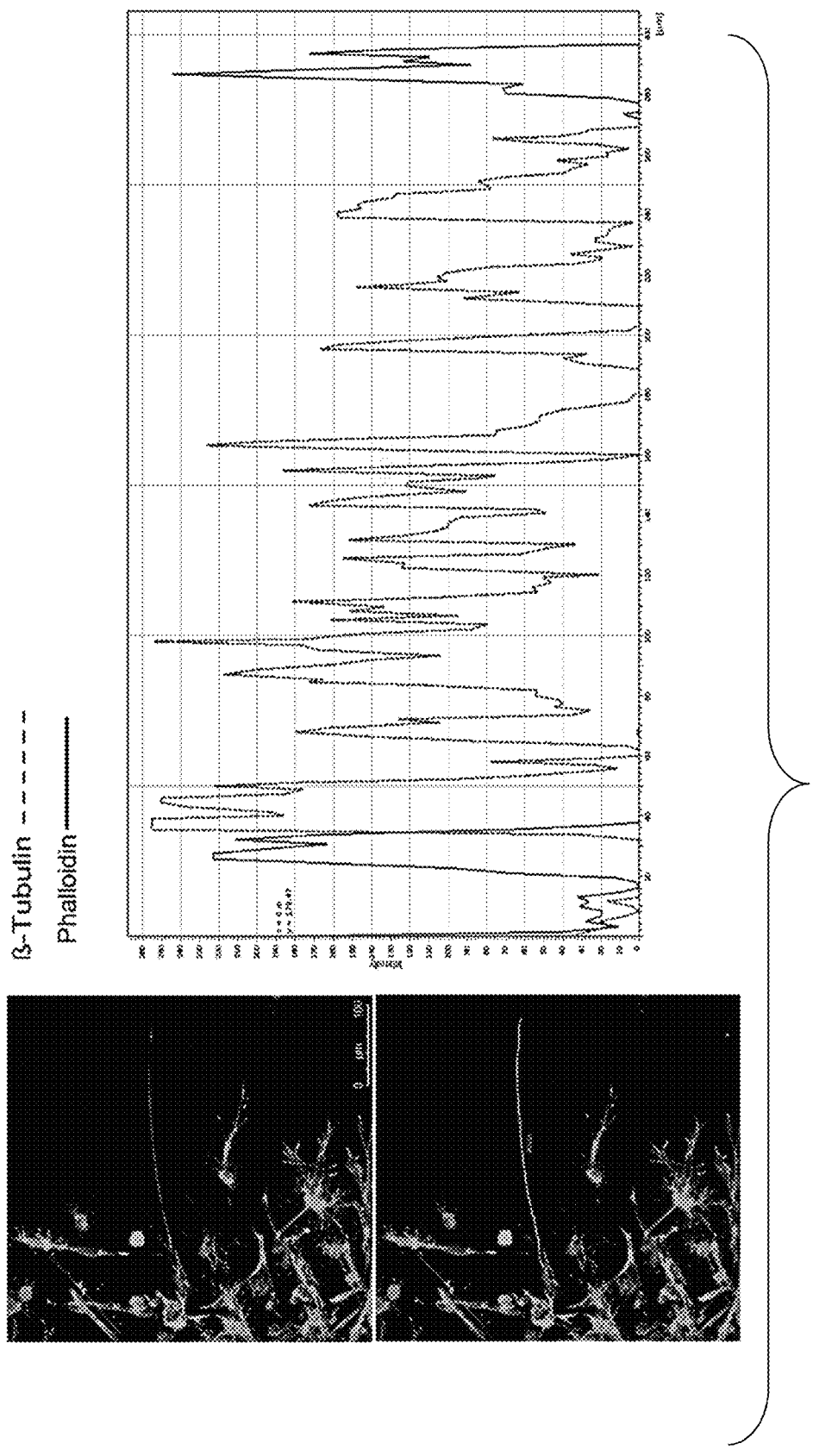
FIGS. 9A-9B: Cytoskeleton-associated protein expression in HGG neurosphere projections. β-tubulin (FIG. 9A), glu-tubulin (FIG. 9B), and F-actin (FIG. 8) expression in patient neurospheres were assessed. Invaded Pat9 neurospheres were fixed after 96 h invasion. Immunofluorescence was performed (left) for indicated proteins and imaged by confocal microscopy using a 63× objective. Tumor TMs were measured on images using Metamorph software by drawing lines (green lines, left) along the length of tumor TMs from cell bodies to the end of the tumor TM to measure the fluorescent intensity of a given fluorescent channel across the line. Histograms of the noted line scan (right) were created for each channel to graph the fluorescent intensities across the length of the TM. "Continuous" expression along a protrusion refers to positive fluorescent value along greater than 50% of line, whereas discontinuous expression is indicated by <50% positive fluorescent values along the drawn line.
Figure 9B:
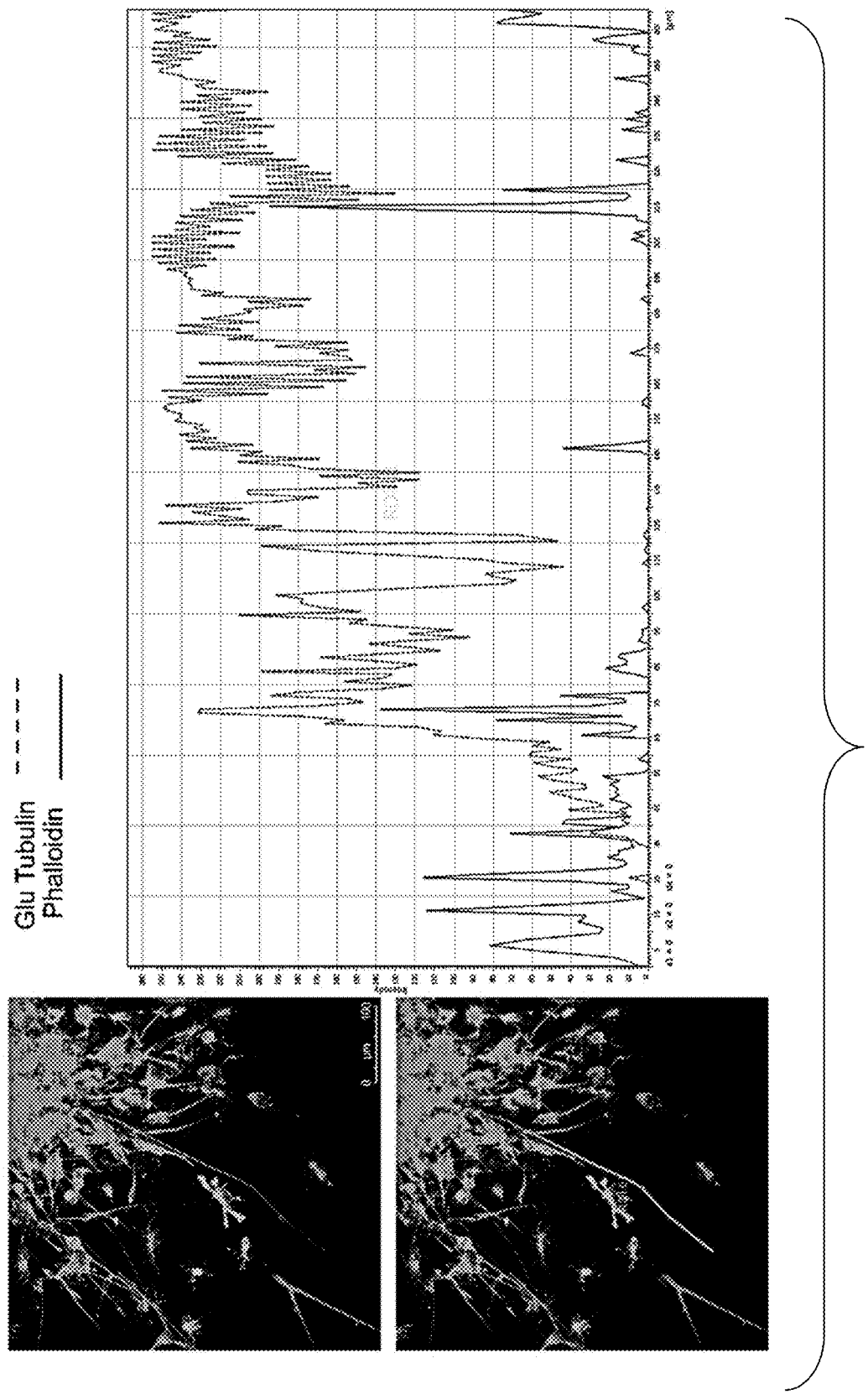
Figure 10:
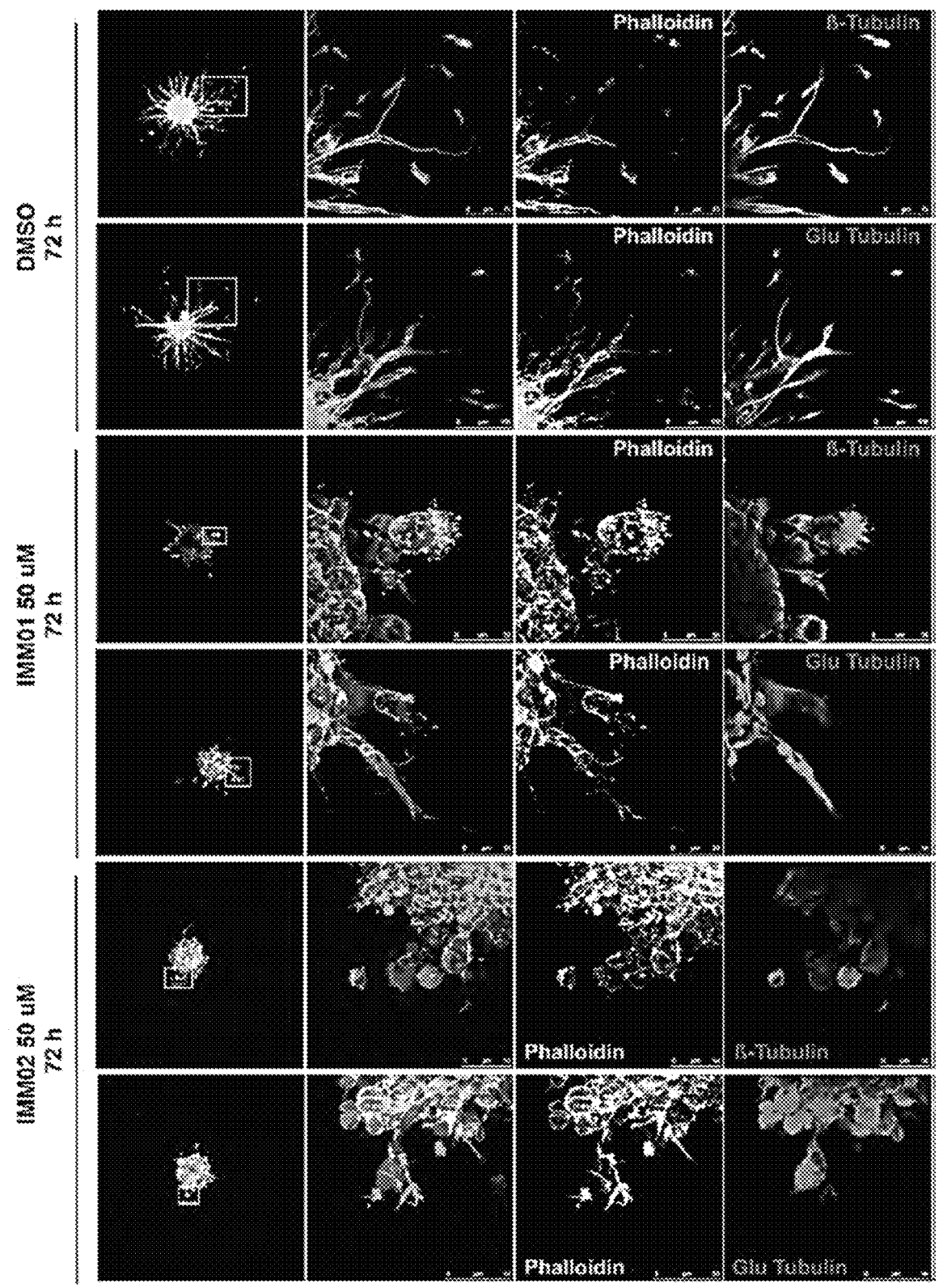
FIG. 10: mDia agonism prevents HGG cell cytoskeleton projections. Confocal imaging of fixed Pat13 invasion assays for F-actin, β-tubulin, or glu-tubulin at the edge of DMSO (top) or 50 μM IMM01 (middle) or IMM02 (bottom)-treated neurospheres. Images are z-stack projections at 72 h invasion.

Interestingly, in control-treated cells, a portion of invaded cells extended cytoskeleton-enriched protrusions into matrigel (FIG. 5A) that measured tens to upwards of several hundreds of microns in length. Control, invaded cells were enriched for enriched for F-actin, β-tubulin, and glu-tubulin. Specifically, the exaggerated cellular projections in the subset of invaded cells revealed F-actin bundles of varying thicknesses and lengths that ran parallel along the protrusions Similar enrichment was seen for β- and glu-tubulin along the projection length. Line scanning was performed using Metamorph software to measure the intensity of cytoskeletal components along cellular protrusions. Cellular projections were traced on images using Metamorph software by drawing lines (green lines, left) along the length of projections from cell bodies to the end of the projection to measure the fluorescent intensity of a given fluorescent channel specifically across the (sub-saturated) line. Continuous expression of a given protein along a protrusion is indicated by a positive fluorescent pixel value along greater than 50% of line, whereas discontinuous expression is indicated by <50% positive fluorescent pixel values along the drawn line. Line scans showed F-actin was discontinuous, while β-tubulin and glu-tubulin were robust and continuous along cellular protrusions (FIGS. 9A-9B, representative images). IMM treatment ablated protrusion formation (FIG. 5B, upper panel), which then re-formed upon drug washout (FIG. 5B, lower panel). The presence of F-actin and glu-tubulin-enriched cellular projections was validated in another HGG patient neurosphere culture, Pat13 (FIG. 1A, FIG. 10), where IMMs inhibited invasion and cellular projection formation.

Figure 6A:
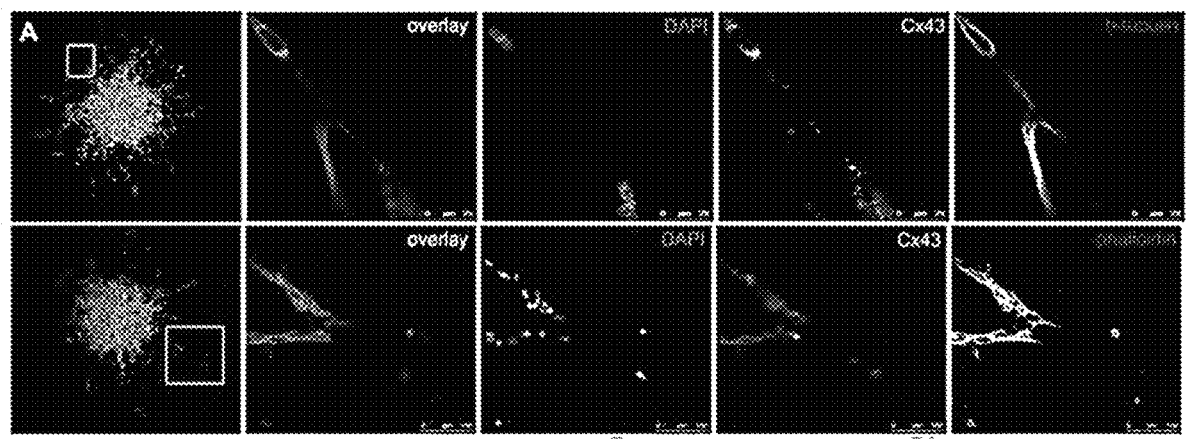
FIGS. 6A-6E: Tumor microtube shortening and amoeboid cell morphologies in IMM-treated HGG patient-derived neurospheres.
Figure 6B:
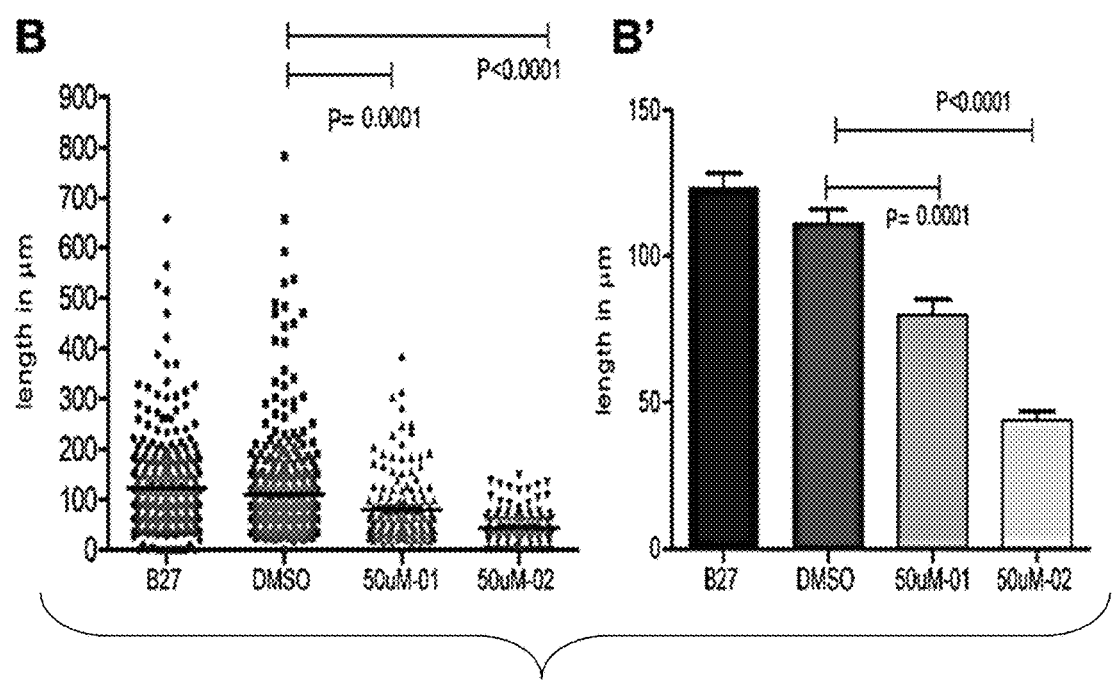
Figure 6C:
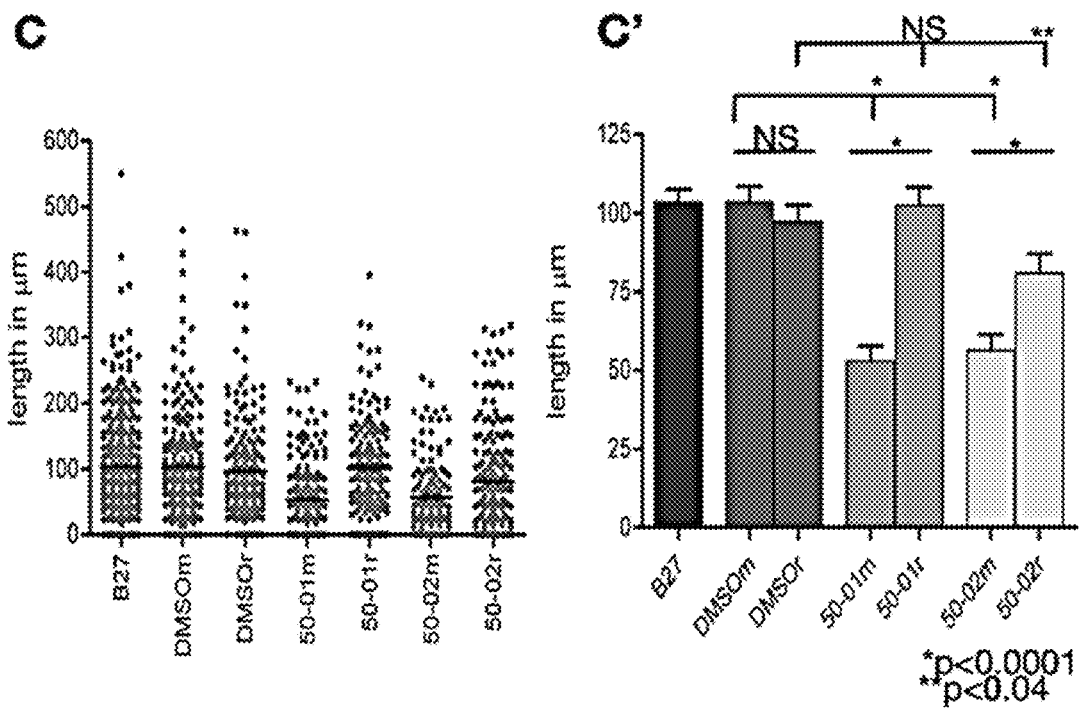
Figure 11:
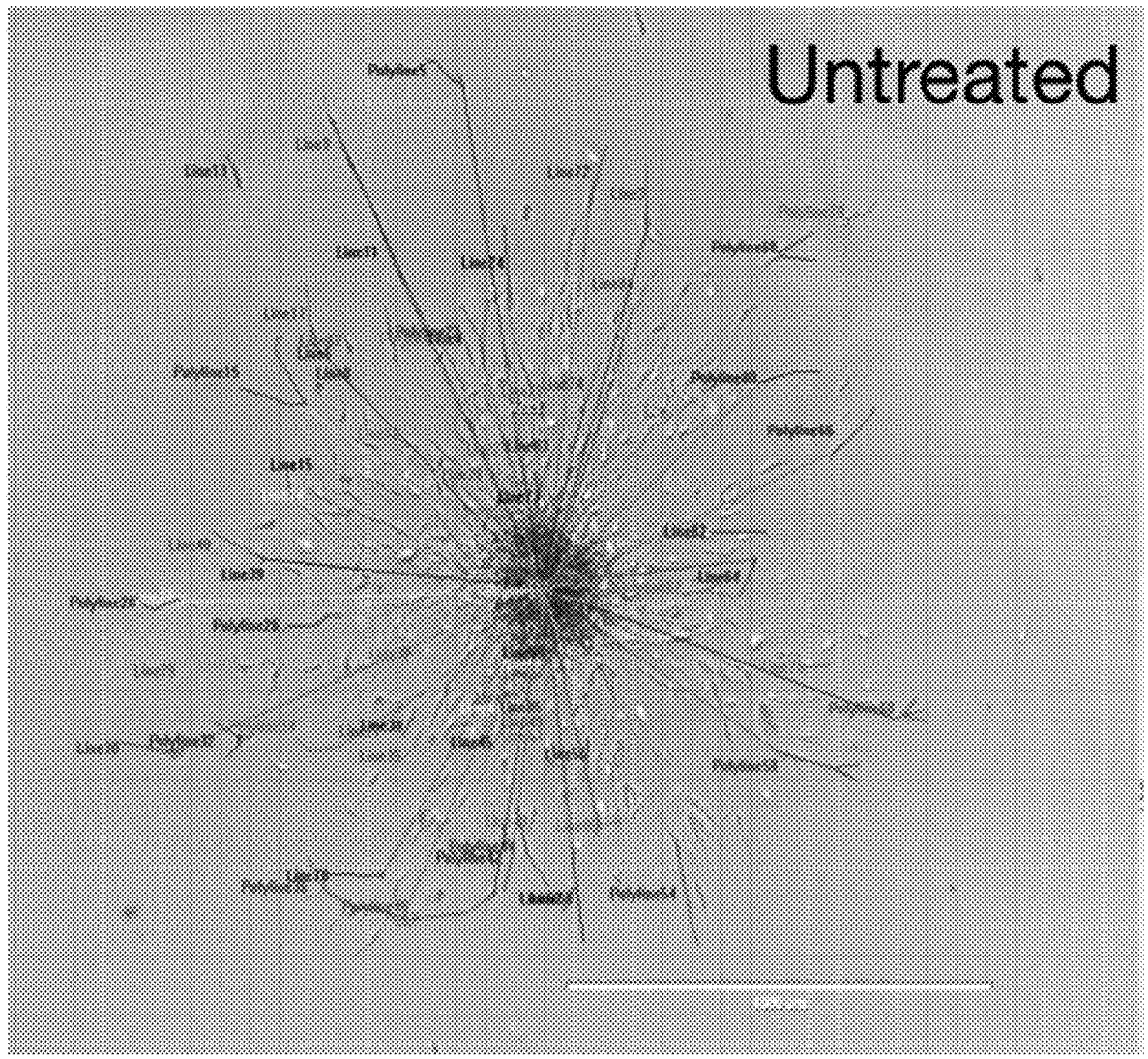
FIG. 11: Tumor TM measurements in HGG patient neurospheres. Pat9 neurospheres invaded for 96 h in matrigel in the presence of DMSO, 50 μM IMM01, or 50 μM IMM02. Tumor TMs were measured using Metamorph software by drawing lines (colored lines) along the length of tumor TMs from cell bodies to the end of the tumor TM using brightfield images.
Figure 11:
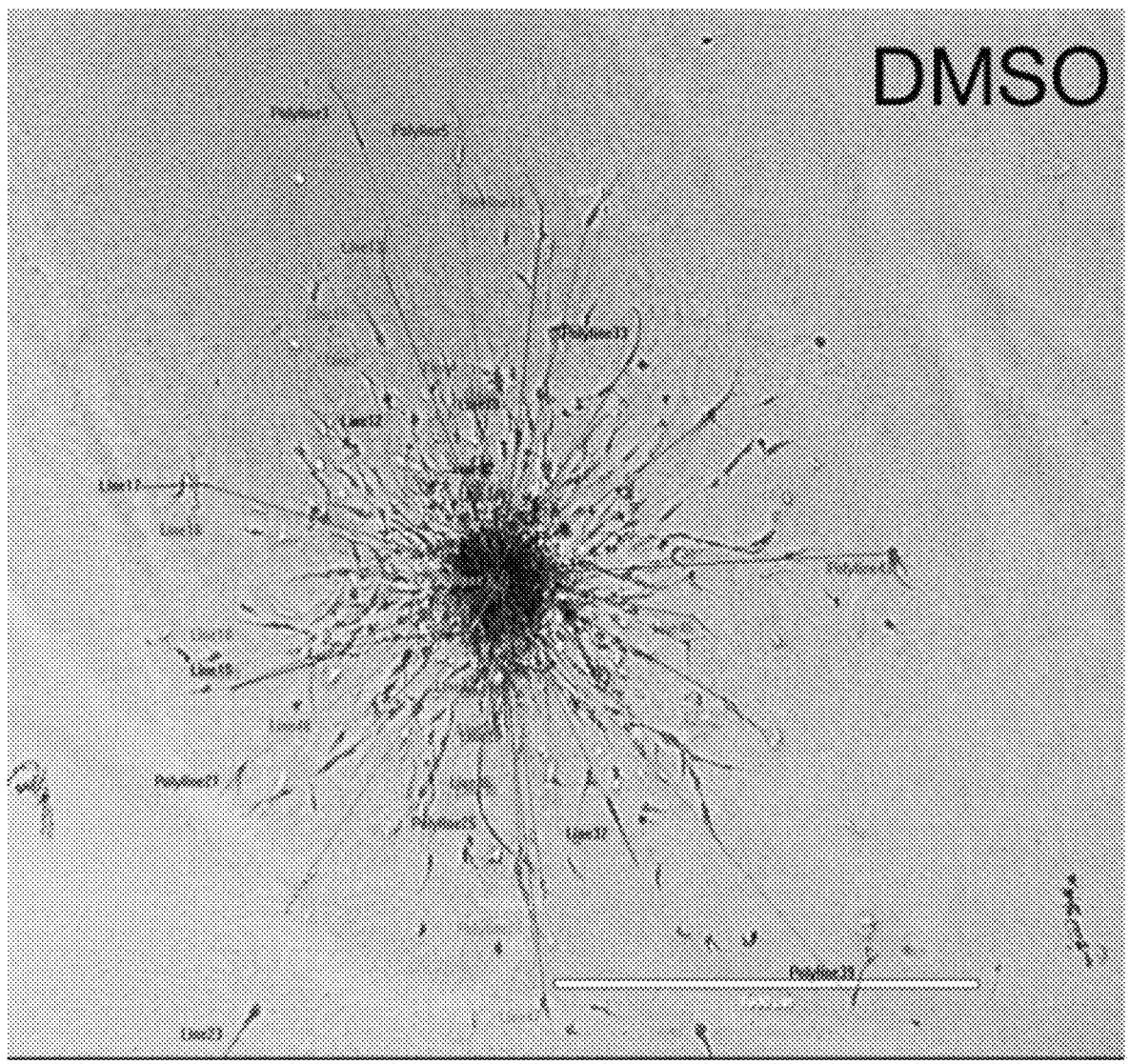
Figure 11:
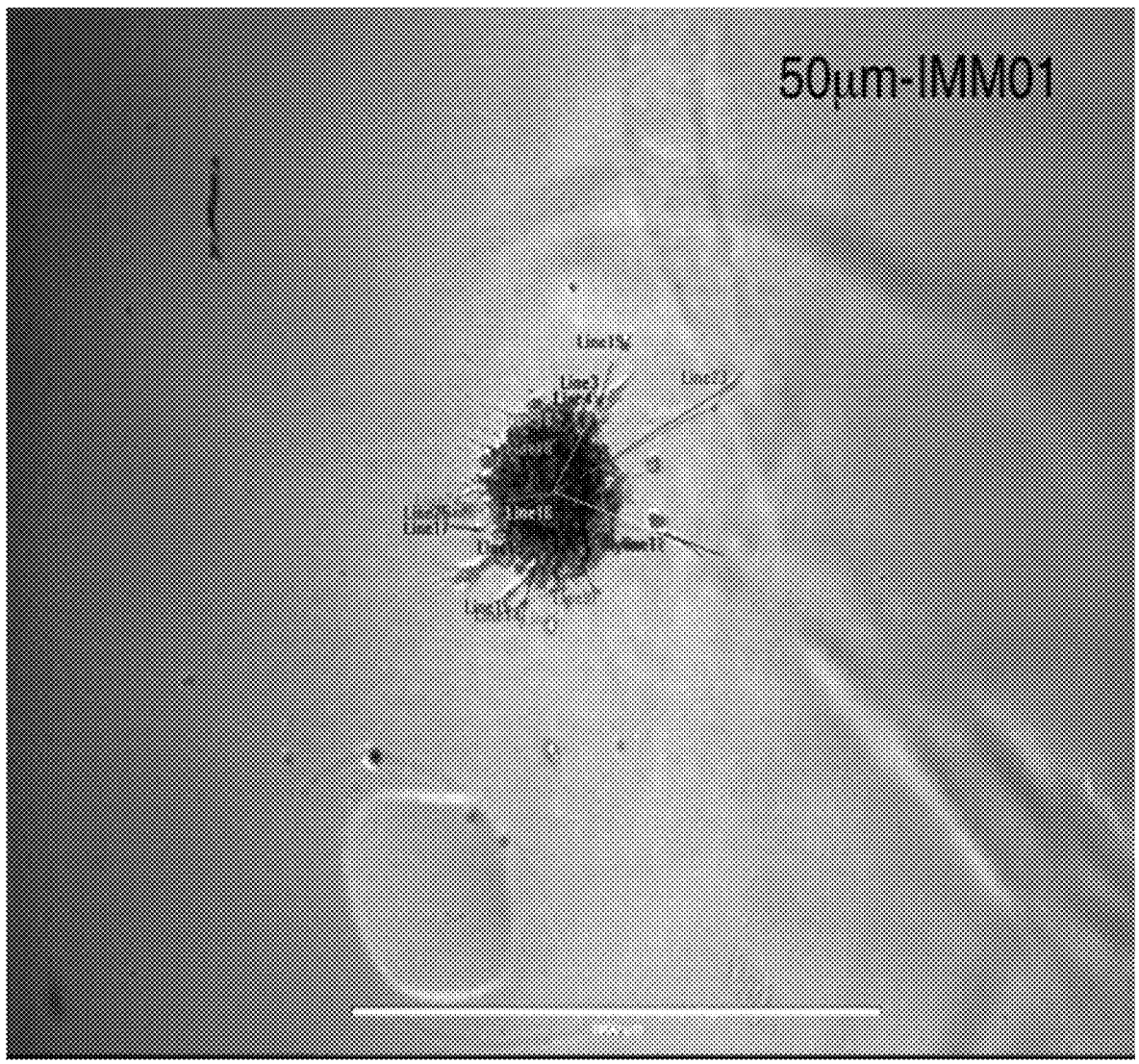
Figure 11:
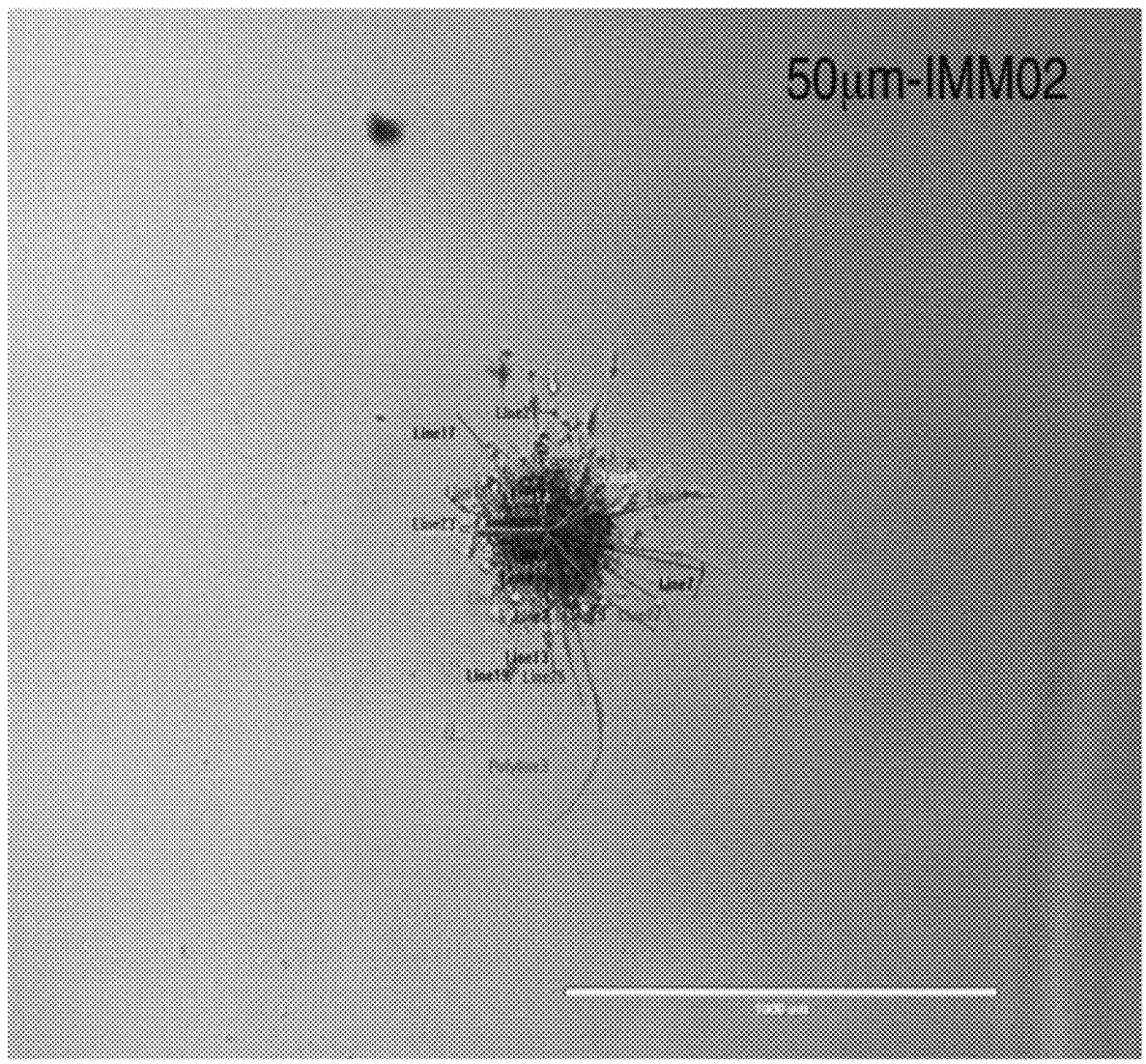

Cell protrusions were confirmed by IF to robustly express punctate Connexin-43 (FIG. 6A). Collectively, the IF revealed these invasive tubulin, F-actin, and Connexin-43-enriched cellular protrusions to be consistent with tumor microtubes (TMs). Tumor TM length was measured in neurosphere edge cells in IMM-treated Pat9 neurospheres. Tumor TM length was shortened from ~125 μm in control edge cells to ~50-75 μm in IMM02- and IMM01-treated cells (FIG. 6b, 11). Tumor TM lengths were recovered to controls upon drug washout (FIG. 6C).

Figure 12A:
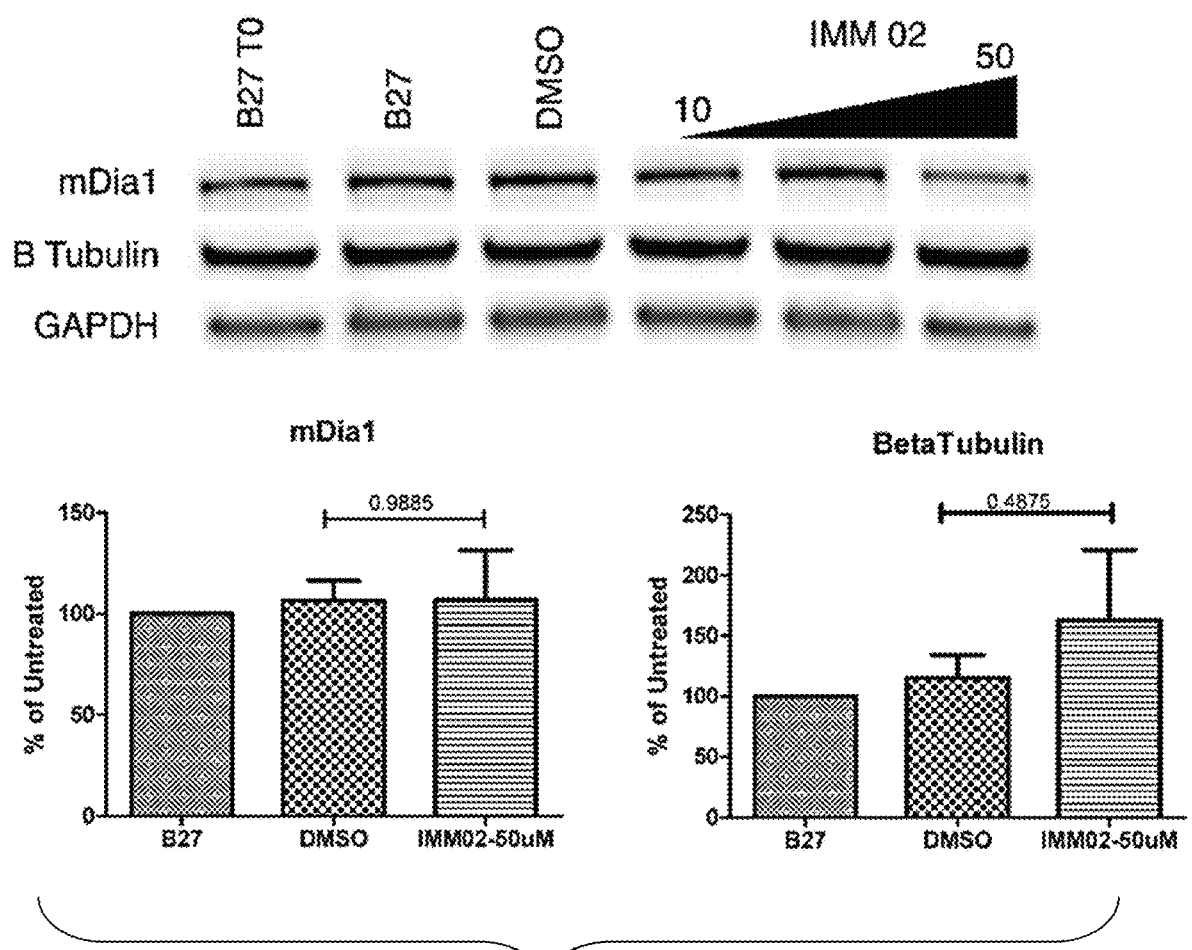
FIGS. 12A-12B: mDia and cytoskeleton protein expression in IMM-treated patient neurospheres. Pat9 monolayers were grown in presence or absence of 10, 20, or 50 μM IMM02, B27 control or DMSO vehicle control for 24 h, or B27 (at T0). Western blotting was performed on cell lysates for mDia1, b-tubulin, and GAPDH as a loading control (FIG. 12A), or mDia2, glu-tubulin, or GAPDH (FIG. 12B). Densitometry was performed on indicated proteins (lower panels), normalizing expression to GAPDH. The experiment was performed in triplicate and standard errors for the averages are shown. p values are indicated.
Figure 12B:
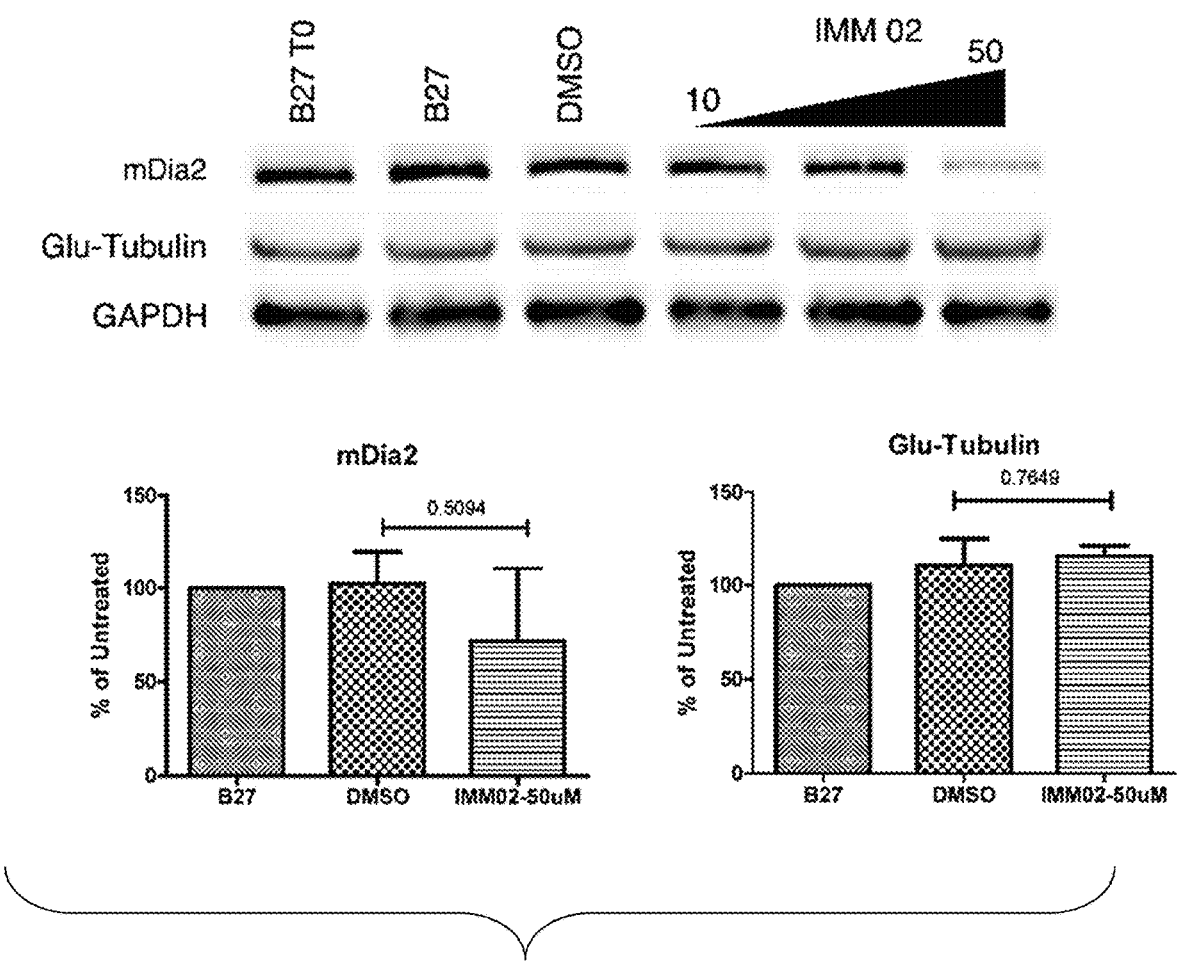
Figure 13:
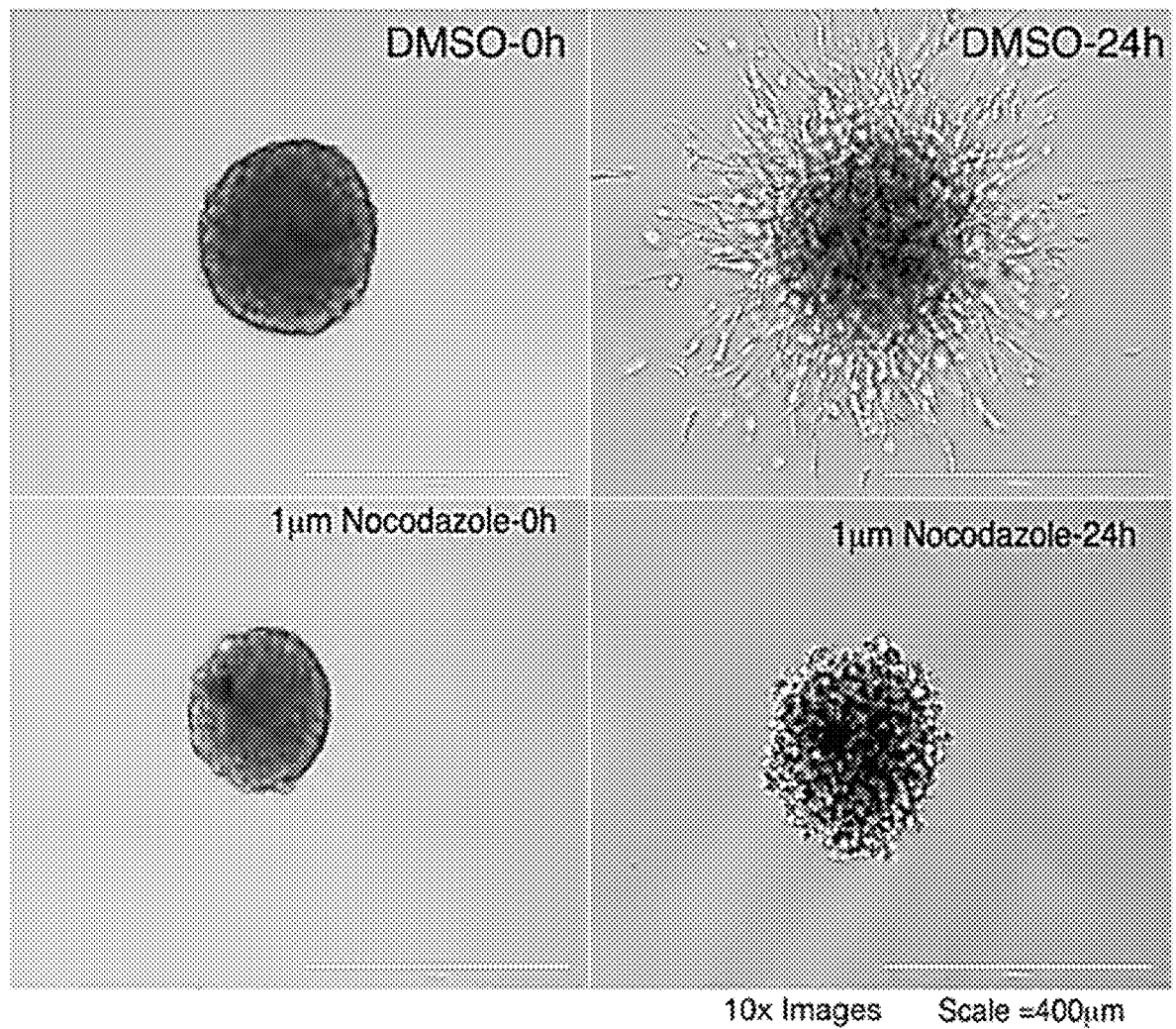
FIG. 13: Requirement for microtubule polymerization in neurosphere invasion and tumor TM formation. Pat9 neurospheres were embedded in matrigel and treated with DMSO or 1 μM nocodazole for 24 h. Images were acquired using brightfield microscopy.

By Western-blotting, IMMs caused a modest, yet not statistically significant, decrease in total cellular mDia2 (and mDia1 to a lesser extent) in Pat9 monolayers at 24 h (FIG. 12), while total β-tubulin and glu-tubulin were slightly increased (also not statistically significant). To confirm dependence of tumor TM formation on microtubules, Pat9 neurospheres were treated with nocadazole to block microtubule polymerization (FIG. 13). Within 24 h, Pat9 invasion and tumor TM formation were halted, indicating a role for microtubules in HGG neurosphere invasion.

mDia Agonism Induces Morphological Plasticity in Invading Neurospheres

Figure 6D:
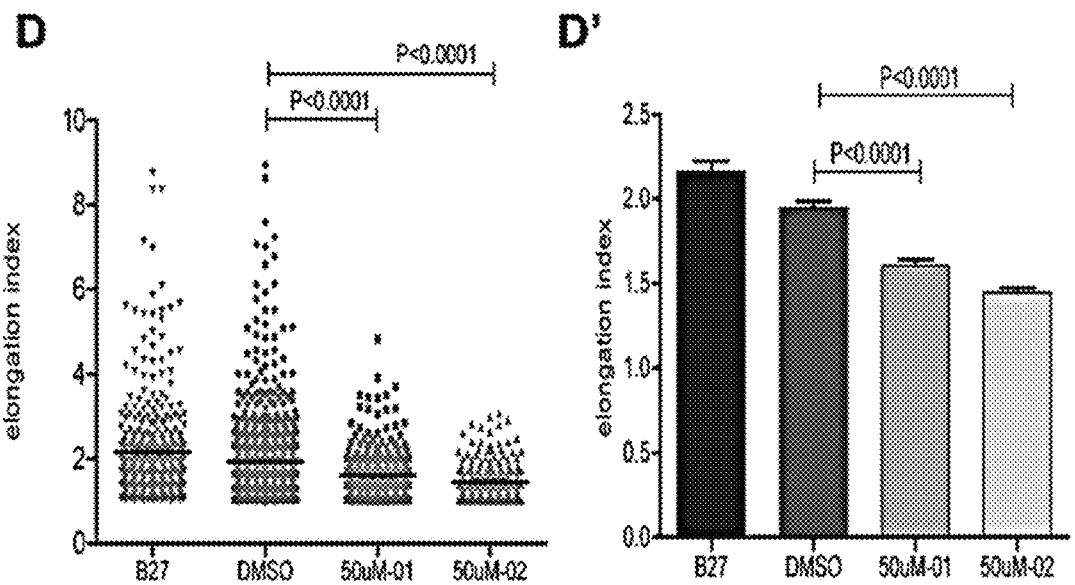
Figure 6E:
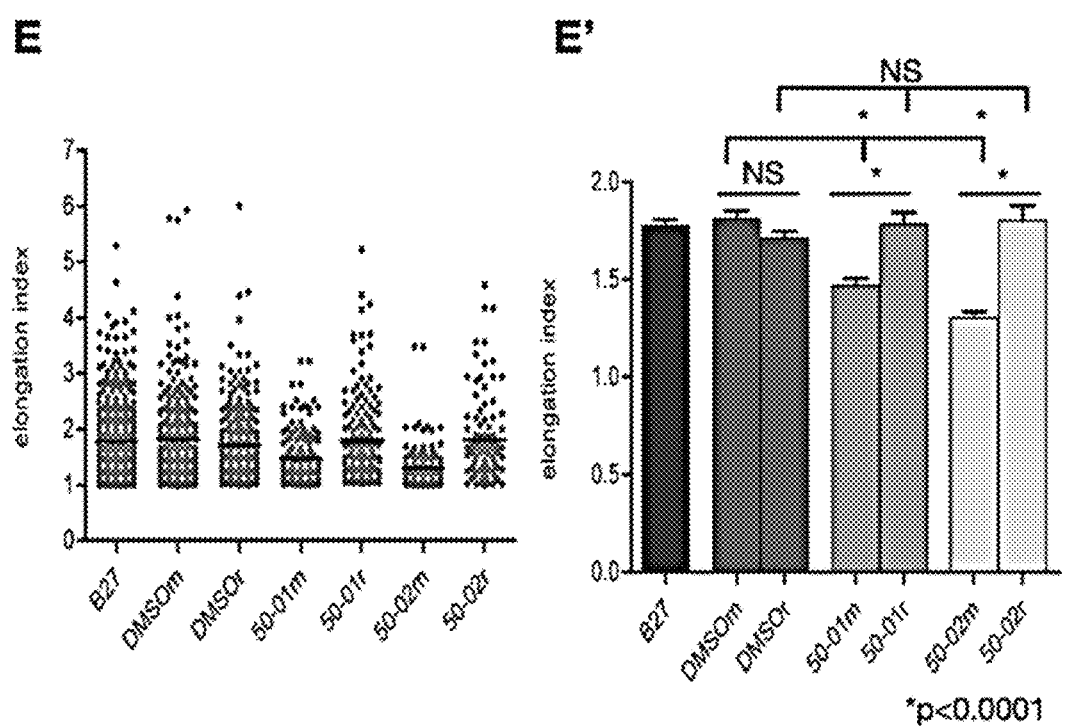

Finally, in IMM-treated neurospheres, a distinct morphological switch occurred (FIGS. 5, 6D) in cells surrounding the edges and was accompanied by tumor TM loss. Cells inter-converted to amoeboid morphologies, as confirmed through elongation index (EI) calculation (long/short axis). Amoeboid cells were generally devoid of cortical F-actin, while enriched in β- and glu-tubulin. Amoeboid morphologies were reversed upon drug washout (FIG. 6E); elongated cell morphologies were recovered and actin and tubulin-enriched tumor TMs were reformed upon washout (FIG. 5). Robust cell motility at the leading invasive edges also resumed (FIG. 5B). Thus, the anti-invasion and anti-tumor TM effects of IMM-mediated mDia agonism are reversible in patient-derived neurospheres.

Discussion

The highly invasive nature of adult high-grade gliomas-specifically GBM-represents a significant and deadly clinical challenge that remains unanswered by current therapeutics. mDia formins play important roles in cell motility and invasion in numerous cancer models, including GBM. Here, mDia expression in primary high-grade gliomas is demonstrated. Using clinically-relevant neurospheres, mDia agonism with IMMs reversibly inhibits in vitro invasion of primary HGGs. IMMs drive a non-motile amoeboid morphological conversion in cells on the edges of HGG neurospheres, and inhibit formation of cytoskeleton and Connexin43-enriched tumor TMs, structures linked to invasiveness and chemoresistance. Thus, mDia agonism effectively disrupted multiple aspects of patient-derived HGG neurosphere invasion.

IMMs effectively blocked invasion in patient-derived neurospheres in multiple IDH1-wild-type high-grade glioma patient samples (FIGS. 3, 9A-9B). Inhibition was reversible, indicating that IMMs as a single agent treatment modality have utility as anti-invasive therapeutics, yet are not cytotoxic as shown with DRAQ7 staining. Interestingly, while IMMs were not cytotoxic when applied to neurospheres at the start of invasion assays, adding IMMs to already invading neurospheres resulted in non-viable neurospheres (FIG. 4C), perhaps indicating a differential susceptibility in targeting formins to invading single cells. In 2D, it was previously demonstrated that there are neither changes in cell cycle progression, nor increases in apoptosis/multinucleation in IMM01/02-treated U251 monolayers. Using monolayer non-transformed NIH3T3s, IMMs impacted cell-cycle progression, while in transformed SW480 colon cancer cells the anti-proliferation effects were less pronounced. However, in 3D, IMMs were neither toxic to normal rat brain tissues, nor to developing zebrafish embryos. IMMs were effective at halting tumor progression in a subset of tumors in animals injected subcutaneously with SW480 colon cancer cells, and in ex vivo rat brain slices, IMMs effectively halted GBM invasion without impacting normal brain tissue.

Longer-term IMM treatment of patient-derived neurospheres may impact cell cycle, and may regulate proliferation to sensitize them to cytotoxic therapeutics. Altered mDia function and/or expression sensitized ovarian and prostate cancer cells to chemotherapy. Breast cancer patients with reduced DIAPH3 expression were more sensitive to taxol and GBM patients with reduced DIAPH3 expression showed reduced survival times. Without wishing to be bound by theory, while these examples focused upon loss of mDia2 function and/or DIAPH3 expression, mDia2 agonism may impact tumor cells similarly, altering cells' ability to drive cytoskeletal dynamics and execute downstream signaling through interacting partners.

Unlike cultured cell lines (i.e., U87, U251), in these examples HGG patient-derived neurospheres revealed tumor TMs extending from a sub-set of leading-edge invading cells (FIGS. 5A-5B-FIGS. 6A-6E). These long protrusions were enriched in stabilized microtubules, F-actin, and Connexin-43, distinguishing them as tumor TMs. Targeting actin and microtubule dynamics (i.e., IMMs, nocodazole) effectively halted invasion and inhibited tumor TMs. Tumor TMs correlated with poor prognosis and radioresistance in IDH1 wild-type GBM histopathological patient samples. Tumor TMs were correlated with GBM invasion in xenografts, and associated with cell-cell communication within the tumor microenvironment via the propagation of intercellular $Ca^{2+}$ waves. Altering mDia function negatively impacted tumor TM formation in the system; mDia agonism targets the F-actin and microtubule cytoskeleton, both of which appear to have roles within tumor TM formation and/or maintenance. Without wishing to be bound by theory, it is believed that mDia2 may direct specific cytoskeletal system dynamics within tumor TMs. Furthermore, without wishing to be bound by theory, it is believed that IMMs may effectively target invasion in this important HGG cell subset.

Finally, morphological plasticity in cells on the edges of IMM-treated neurospheres was unexpectedly observed (FIGS. 6A-6E). Invasion was weak and amoeboid shaped cells detached from the neurosphere itself. mDia inhibition via expression of dominant negative constructs or siRNA, or treatment with SMIFH2, induced amoeboid morphological conversions in a variety of epithelial cancers, including ovarian, prostate, breast, and hepatocarcinoma. Without wishing to be bound by theory, one possible explanation for this morphological conversion is that with disrupted mDia dynamic activation, RhoA/ROCK1 contractility/disruption of cell-cell adhesions may be favored, leading to sustained leading edge contraction that drives cellular extrusion. Interestingly, these amoeboid cells do not migrate far from the edge (FIGS. 5A-5B). conversions in a variety of epithelial cancers, including ovarian, prostate, breast, and hepatocarcinoma. Without wishing to be bound by theory, one possible explanation is that it is possible that ROCK activation alone is not sufficient to drive motility in these cells, as mDia2 has critical roles in amoeboid-based motility through RhoA/C-directed non-apoptotic bleb retraction and re-establishment of the F-actin cortex. Thus, IMMs combined with ROCK inhibition may be an effective anti-invasion strategy in HGG patient-derived neurospheres.

Materials and Methods

Cell Culture

U87 were a kind gift from Dr. William Maltese and Jean Overmeyer (University of Toledo). U251 cells were a kind gift from Martha Howard (University of Toledo). GBM cells were maintained in DMEM (HyClone) with 10% FBS (vol/vol) (Atlantic Biological), 100 U/ml penicillin, and 100 mg/ml streptomycin (Gibco) in a 37° C. humidified incubator with 5% $CO_2$.

Cell Isolation and Cryofreezing

All subjects gave their informed consent for inclusion before they participated in the study. The study was conducted in accordance with the declaration of Helsinki, and the protocol was approved by the University of Toledo Institutional Review Board (IRB #201913). De-identified surgical samples were collected from the University of Toledo Medical Center or ProMedica Toledo Hospital using a joint consent form. Resected tumors were transported in PBS on ice. Single-cell isolation was performed as described with minor modifications. Briefly, tumors were washed with D-PBS and photographed with an iPhone7 camera. Tumors were minced with surgical scalpels. For cell isolation, a portion of minced tumors were placed in 15 mls of 0.05% trypsin (Gibco) and rotated at 37° C. for at least 45 min. Tumors were triturated, and tissue returned to 37° C. with rotation. Trypsin was neutralized in equal volumes of Neural Basal Media/10% FBS. After 5 min room-temperature (RT) incubation, cells were centrifuged at 1000 rpm for 5 min and resuspended in 10 mls of ice-cold Red Blood Cell Lysis Buffer (0.15 M $NH_4Cl$, 10 mM $NaHCO_3$, and 0.1 mM EDTA). This reaction was neutralized with equal volumes ice-cold DPBS (HyClone). Cells were centrifuged at 250×g for 5 min, resuspended in Neural Basal Media (Gibco) supplemented with 1×B27 (Gibco), 20 ng/ml bFGF and EGF (Peprotech), 1× Sodium Pyruvate, 1× GlutaMax, and 1× Anti-Anti (Gibco). Cells were strained through 70 µM strainers (Fisher Scientific) and plated into 6-well tissue culture plates (USA Scientific). Media was changed after 24 h.

For cryo-freezing and cell recovery, minced tissue was placed in cryotube (Greiner) with full media and 10% DMSO (Fisher Scientific) and placed in a freezing container (Nalgene) that lowers the temperature 1°/min. Tissues were placed at −80° C. overnight, and moved to −150° C.

Neurosphere Formation and Culture

Neurospheres formed spontaneously in isolated patient sample monolayer cells. Once spheres detach from monolayers, they were collected using wide-orifice pipette tips and moved to poly-HEMA (Sigma) coated U-bottom 96-well plates. Neurospheres were used upon reaching 200-250 µm diameter. Once neurospheres reached 350 µm, they were dissociated and re-plated in poly-HEMA U-bottom plates at 2000 cells/well.

Invasion Assays 3D invasion assays were as described. Briefly, a thin layer of 5 mg/ml GFR matrigel (Corning) was placed in 8-well chamber glasses (Lab-tek). Neurospheres were added and topped with thin-layer matrigel. Matrigel polymerized for 45 min at 37° C. before addition of 250 µl of media with IMMs. Invasions were imaged at time zero (T0) and every 24 h for experimental durations. Invaded spheroids/spontaneous neurospheres were imaged using an EVOS inverted microscope with an Olympus 4×UplanFL N0.13 PhP objective lens. All measurements were completed with MetaMorph software (Molecular Devices).

Immunofluorescence (IF)

Draq7 (Abcam) was loaded into neurospheres as described. For 3D IF, neurospheres were stained as described, with modifications. Invasions were fixed in 4% paraformaldehyde/PBS for 20 min at RT. Chambers were permeabilized with 0.5% Triton X-100/PBS (Sigma) for 60 min at RT. Chambers were washed in PBS-T (PBS with 0.1% Triton X-100) and blocked in 3% BSA for 1 hr at RT. mDia2 and mDia1 (1:100) or Connexin-43 (1:200) (Proteintech), β-Tubulin (1:100) (Sigma), Glu-Tubulin (1:100) (Millipore Sigma) antibodies were incubated at 4° C. for 48-72 h. Invasions were washed with PBS-T before adding AlexaFluor 2° antibodies (1:200-500), AlexaFluor Phalloidin (1:100), or DAPI (1:50) (Molecular Probes) for 24-48 h at 4° C. The wells were imaged on a Leica TCS SP5 multiphoton laser-scanning confocal microscope. Optical slices of 2.5 µm were acquired in Z-stacks using a Leica 10×Pl Apo CS Dry 0.40 NA objective.

For 2D IF, cells were processed as described. Cells were plated on coverslips, fixed in 4% paraformaldehyde/PBS for 5 min at RT, permeabilized with 0.2% Triton X-100 for 20 min before incubating with antibodies: mDia1, mDia2, Ki67 (1:200) (Origene), β-Tubulin (1:200) (Sigma), and Glu-Tubulin (1:200) (Millipore) were incubated ON at 4° C. Coverslips were incubated ON at 4° C. with (1:500) AlexaFluor 2° antibodies, (1:500) AlexaFluor phalloidin and (1:100) DAPI. Coverslips were washed in PBS, followed by deionized-water, and were mounted to slides with Fluoromount-G (Southern Biotech). Coverslips were imaged on a Leica TCS SP5 multiphoton laser-scanning confocal microscope using 2.5 µm optical slices assembled into Z-stacks using a Leica 40×HCX Pl Apo CS Oil 1.25-0.75 NA objective or a 63×HCX Pl Apo CS Oil 1.4-0.6 NA objective.

Western Blotting

Confluent cell monolayers were lysed (0.5M Tris-HCL pH 6.8, glycerol, 10% (w/v) SDS, and bromophenol blue supplemented with dithiothreitol (DTT)). Lysates were quantified by BioRad DC Protein Assay, loaded into a 4-20% mini-protean TGX gel (BioRad), and transferred to PVDF membranes (BioRad) (Trans Blot Turbo System (BioRad)) then blocked in 5% non-fat dry milk mDia1, mDia2, Glu-tubulin, β-tubulin, and GAPDH (Proteintech) antibodies were incubated ON at 4° C. Blots were washed with TBST and peroxidase-conjugated 2° antibodies (Jackson ImmunoResearch) were incubated at RT for 90 min. Blots were imaged on a Syngene Western Blot Imager.

Statistical Analysis

Analyses were performed using GraphPad software. ANOVA or Students t-tests were performed to assess statistical significance, as indicated. A p value<0.05 was statistically significant.

CONCLUSIONS

In conclusion, roles for mDia2 in regulating the dynamic cytoskeleton in support of tumor TM-directed invasive adult high-grade glioma patient-derived neurospheres have been discovered. IMM agonists effectively halt invasion, while suppressing tumor TM formation and eliciting a distinct amoeboid morphological transition in tumor cells. These examples illustrate a clinically-relevant role mDia2 plays in HGG invasion.

Certain embodiments of the compositions and methods disclosed herein are defined in the above examples. It should be understood that these examples, while indicating particular embodiments of the invention, are given by way of illustration only. From the above discussion and these examples, one skilled in the art can ascertain the essential characteristics of this disclosure, and without departing from the spirit and scope thereof, can make various changes and modifications to adapt the compositions and methods described herein to various usages and conditions. Various changes may be made and equivalents may be substituted for elements thereof without departing from the essential scope of the disclosure. In addition, many modifications may be made to adapt a particular situation or material to the teachings of the disclosure without departing from the essential scope thereof.

What is claimed is:

1. A method of inhibiting high-grade glioma (HGG) patient neurosphere invasion, the method comprising:
   administering an effect amount of a mammalian Diaphanous (mDia) agonist to a patient having HGG, and inhibiting HGG neurosphere invasion in the patient;
   wherein the mDia agonist comprises IMM01 or IMM02;
   wherein IMM01 is 2-[(2,4-dihydroxyphenyl)methylene]-N-(1,1-dimethylethyl)-hydrazinecarbothioamide, having formula (1):

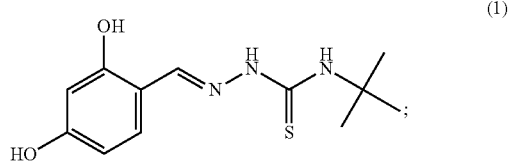 [SMILES: CC(C)(C)NC(=S)N/N=C/c1ccc(O)cc1O]

and
   wherein IMM02 is N1-(tert-butyl)-2-[1-(3,5-difluoro-2-hydroxyphenyl)ethylidene]hydrazine-1-carbothioamide, having formula (2):

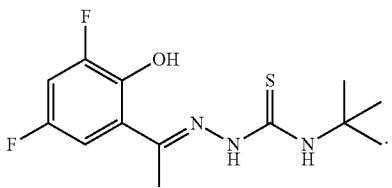

(2)

2. The method of claim 1, wherein the mDia agonist comprises a combination of IMM01 and IMM02.

3. The method of claim 1, wherein the effective amount ranges from about 10 μM to about 50 μM.

4. The method of claim 1, wherein the HGG is chemoresistant or radioresistant.

5. The method of claim 1, wherein the mDia agonist is administered in a combination therapy with a Rho-associated protein kinase (ROCK) inhibitor.

6. The method of claim 1, wherein the mDia agonist is an agonist of mDia1.

7. The method of claim 1, wherein the mDia agonist is an agonist of mDia2.

8. A method of treating a brain tumor, the method comprising:
 administering an effective amount of a mDia agonist to a patient having a brain tumor, and
 treating the brain tumor;
 wherein the mDia agonist comprises IMM01 or IMM02;
 wherein IMM01 is 2-[(2,4-dihydroxyphenyl)methylene]-N-(1,1-dimethylethyl)-hydrazinecarbothioamide, having formula (1):

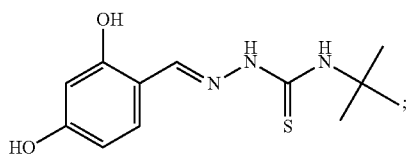

(1)

and
 wherein IMM02 is N1-(tert-butyl)-2-[1-(3,5-difluoro-2-hydroxyphenyl)ethylidene]hydrazine-1-carbothioamide, having formula (2):

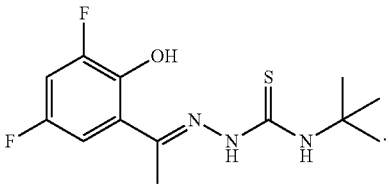

(2)

9. The method of claim 8, wherein the mDia agonist comprises a combination of IMM01 and IMM02.

10. The method of claim 8, wherein the effective amount ranges from about 10 μM to about 50 μM.

11. The method of claim 8, wherein the HGG is chemoresistant or radioresistant.

12. The method of claim 8, wherein the mDia agonist is administered in a combination therapy with a Rho-associated protein kinase (ROCK) inhibitor.

13. The method of claim 8, wherein the mDia agonist is an agonist of mDia1.

14. The method of claim 8, wherein the mDia agonist is an agonist of mDia2.

15. The method of claim 8, wherein treatment render brain tumor cells sensitive to chemotherapy or radiation.

16. The method of claim 8, wherein treatment halts tumor microtubule (TM) formation, invasion, or proliferation in the patient.

17. The method of claim 8, wherein treatment induces cell death in invading brain tumor cells.

* * * * *